(12) United States Patent
Amini et al.

(10) Patent No.: US 10,159,971 B2
(45) Date of Patent: Dec. 25, 2018

(54) APPARATUS AND METHOD FOR ECONOMIC, FAST AND EASY SAMPLING OF FOOD AND ENVIRONMENTAL SAMPLES

(71) Applicant: Clear Labs Inc., Menlo Park, CA (US)

(72) Inventors: Sasan Amini, Redwood City, CA (US); Eugene Kane, II, North Canton, OH (US); Mahni Ghorashi, Belmont, CA (US); Kaveh Milaninia, San Jose, CA (US)

(73) Assignee: Clear Labs Inc., Menlo Park, CA (US)

( * ) Notice: Subject to any disclaimer, the term of this patent is extended or adjusted under 35 U.S.C. 154(b) by 235 days.

(21) Appl. No.: 15/143,605

(22) Filed: May 1, 2016

(65) Prior Publication Data

US 2017/0113216 A1 Apr. 27, 2017

Related U.S. Application Data

(60) Provisional application No. 62/156,308, filed on May 3, 2015, provisional application No. 62/234,104, filed on Sep. 29, 2015.

(51) Int. Cl.
*B01L 3/02* (2006.01)
*G01N 35/10* (2006.01)
(Continued)

(52) U.S. Cl.
CPC ........... *B01L 3/0217* (2013.01); *B01L 3/0275* (2013.01); *G01N 1/08* (2013.01); *G01N 1/14* (2013.01);
(Continued)

(58) Field of Classification Search
CPC .......... B01L 3/02; B01L 3/021; B01L 3/0213; B01L 3/0217; B01L 3/022; G01N 35/10; G01N 1/08
See application file for complete search history.

(56) References Cited

U.S. PATENT DOCUMENTS 2,463,455 A * 3/1949 Morris .................. C12M 25/14
30/128
2,525,604 A * 10/1950 Johnson ............... A22C 29/025
408/204
(Continued)

FOREIGN PATENT DOCUMENTS

WO WO 0057153 A1 * 9/2000 ................ B26F 1/16

*Primary Examiner* — David A Rogers
(74) *Attorney, Agent, or Firm* — IP Law Leaders PLLC

(57) ABSTRACT

A handheld solid sample pipette device includes a pipette tube with a number of sharpened teeth adapted to pierce solid or substantially solid sample material, the pipette tube adapted to be matingly attached to a device that includes a handle, a plunger, and a piston within a shell of the device. A spring may be positioned to return the plunger to a non-depressed position following depression of the plunger. A sample of the material can be ejected from the handheld device. The handheld device may further include a shear ring apparatus, that in-turn includes a tube portion, a plurality of shear ring teeth, and a knobbed plate for rotating the shear ring. Following insertion of the pipette with sharpened teeth into the sample, the shear ring apparatus is pressed into the sample as well, such that the shear ring tube, which is slidingly engaged about the pipette tube, slides over the pipette tube into the sample. The shear ring teeth pierce the sample, and at a certain point of insertion, the shear ring apparatus is rotated in either or both a clockwise or counter-clockwise manner such that the shear ring teeth sever a portion of the material to be sampled such that the portion remains within the pipette tube, for removal, and analysis.

22 Claims, 21 Drawing Sheets

(51) Int. Cl.
   *G01N 1/08* (2006.01)
   *G01N 1/14* (2006.01)
(52) U.S. Cl.
   CPC ........... *B01L 2200/0647* (2013.01); *B01L 2200/0657* (2013.01); *B01L 2300/0672* (2013.01); *B01L 2400/0478* (2013.01); *G01N 35/1065* (2013.01); *G01N 2001/1418* (2013.01)

(56) References Cited

U.S. PATENT DOCUMENTS

| | | | | |
|---|---|---|---|---|
| 2,987,922 A * | 6/1961 | Harrington | ............ | G01N 1/08 73/864.44 |
| 3,252,331 A * | 5/1966 | Lancaster | ............ | B01L 3/02 222/356 |
| 4,310,969 A * | 1/1982 | Cannizzaro | ............ | A47J 25/00 30/113.1 |
| 4,464,941 A * | 8/1984 | Herold | ............ | B01L 3/0217 222/386 |
| 4,734,261 A * | 3/1988 | Koizumi | ............ | B01L 3/0217 141/243 |
| 4,862,753 A * | 9/1989 | Lovette | ............ | B01L 3/02 422/919 |
| 5,005,433 A * | 4/1991 | Patton | ............ | E21B 25/005 73/863 |
| 5,104,624 A * | 4/1992 | Labriola | ............ | B01L 3/0224 141/25 |
| 5,324,300 A * | 6/1994 | Elias | ............ | A61B 10/025 606/179 |
| 5,587,062 A * | 12/1996 | Togawa | ............ | G01N 27/44739 204/456 |
| 5,697,935 A * | 12/1997 | Moran | ............ | A61B 17/8875 408/204 |
| 5,794,344 A * | 8/1998 | Poulos | ............ | A47J 25/00 30/113.1 |
| 5,865,259 A * | 2/1999 | Catto | ............ | A01B 1/065 172/22 |
| 5,954,671 A * | 9/1999 | O'Neill | ............ | A61B 17/1637 600/567 |
| 6,035,750 A * | 3/2000 | Hansen | ............ | B26D 7/1863 30/124 |
| 6,223,637 B1 * | 5/2001 | Hansen | ............ | B26D 7/1863 30/124 |
| 6,482,361 B1 * | 11/2002 | Suovaniemi | ............ | B01L 3/0217 422/525 |
| 6,565,728 B1 * | 5/2003 | Kozulic | ............ | B26D 7/1818 204/606 |
| 6,702,990 B1 * | 3/2004 | Camacho | ............ | B01L 3/0217 204/613 |
| 6,945,942 B2 * | 9/2005 | Van Bladel | ............ | A61B 18/02 600/567 |
| 7,059,207 B2 * | 6/2006 | Harris | ............ | G01N 1/08 73/864.45 |
| 7,093,508 B2 * | 8/2006 | Harris | ............ | B01L 99/00 73/864 |
| 7,361,308 B2 * | 4/2008 | Fagerstam | ............ | G01N 27/44717 204/606 |
| 7,866,223 B2 * | 1/2011 | Jenkins | ............ | G01N 1/08 408/204 |
| 7,943,393 B2 * | 5/2011 | Gjerde | ............ | G01N 35/10 436/178 |
| 8,524,170 B2 * | 9/2013 | Petrek | ............ | B01L 3/022 422/500 |
| 2003/0037440 A1 * | 2/2003 | Raz | ............ | A47J 25/00 30/113.1 |
| 2005/0044971 A1 * | 3/2005 | Harris | ............ | G01N 1/04 73/864.43 |
| 2005/0066751 A1 * | 3/2005 | Harris | ............ | G01N 1/08 73/864.45 |
| 2015/0355149 A1 * | 12/2015 | Schulz | ............ | G01N 30/91 73/61.55 |
| 2016/0041071 A1 * | 2/2016 | Bruehwiler | ............ | G01N 1/08 73/61.59 |

* cited by examiner

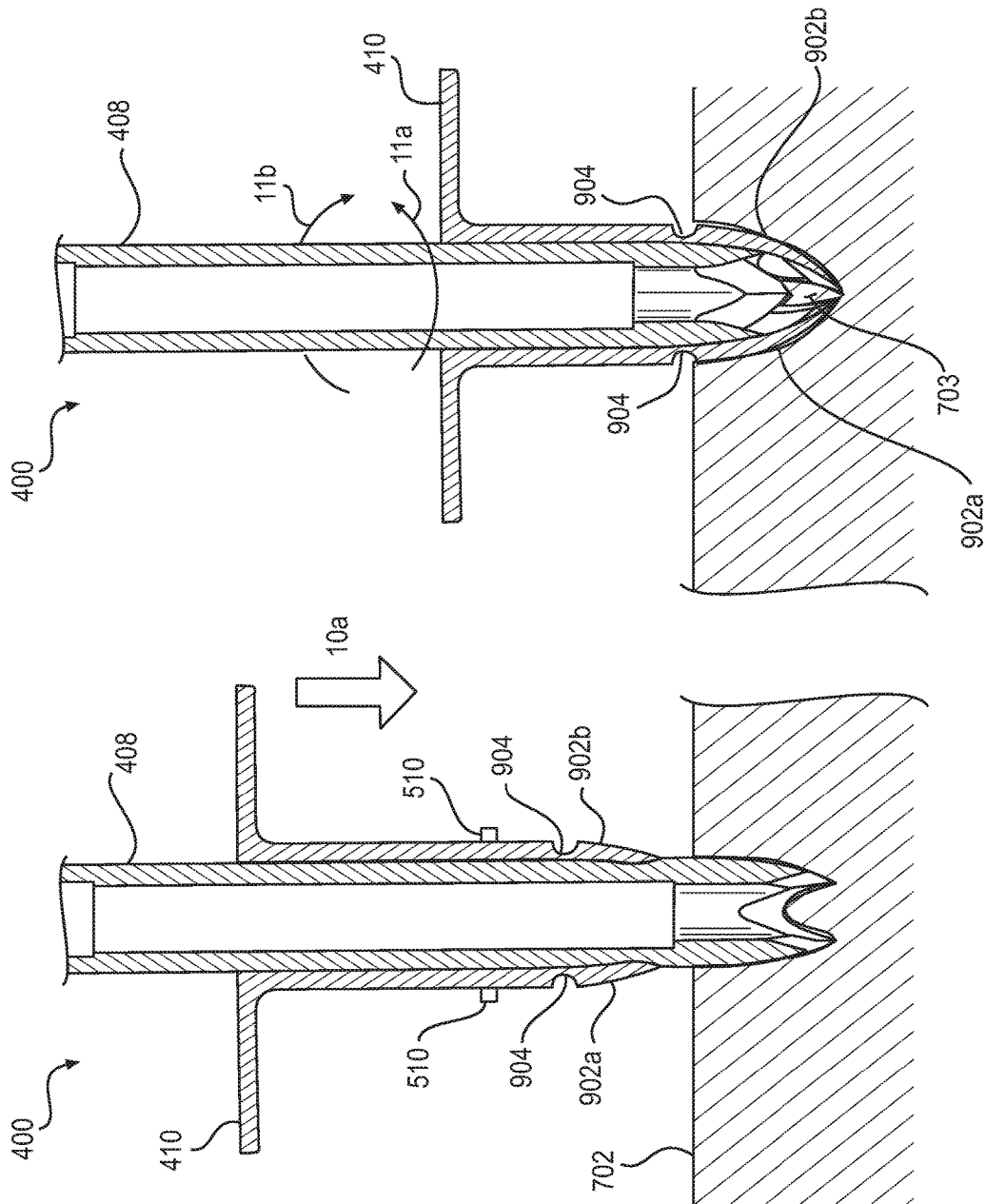

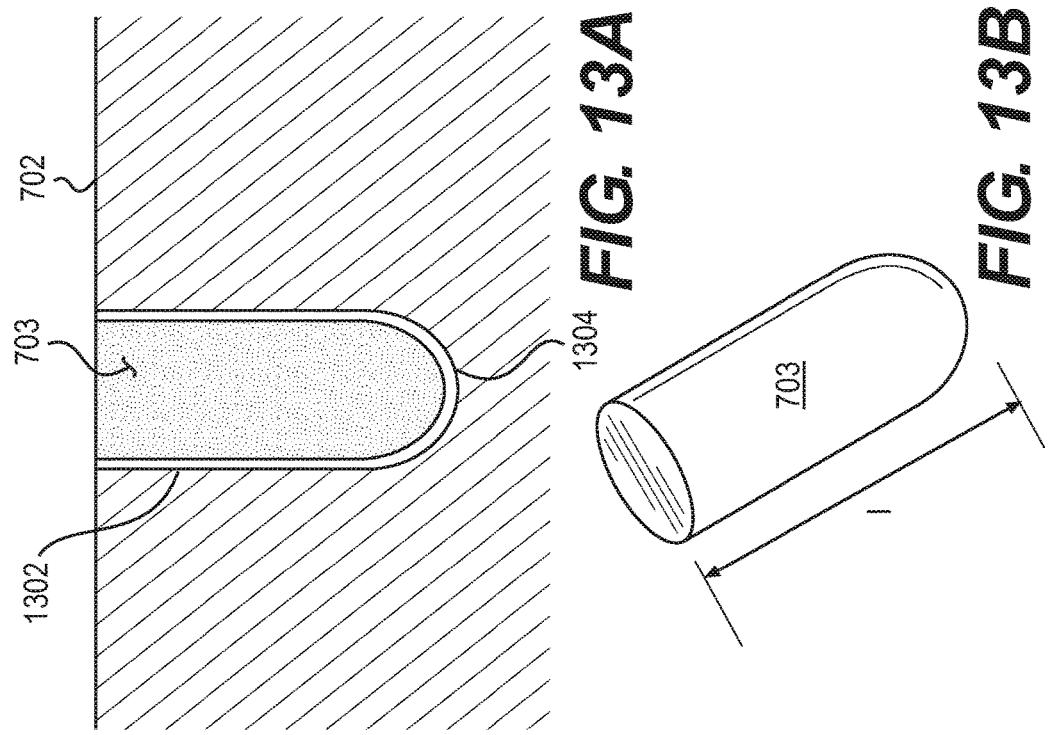
FIG. 13A
FIG. 13B
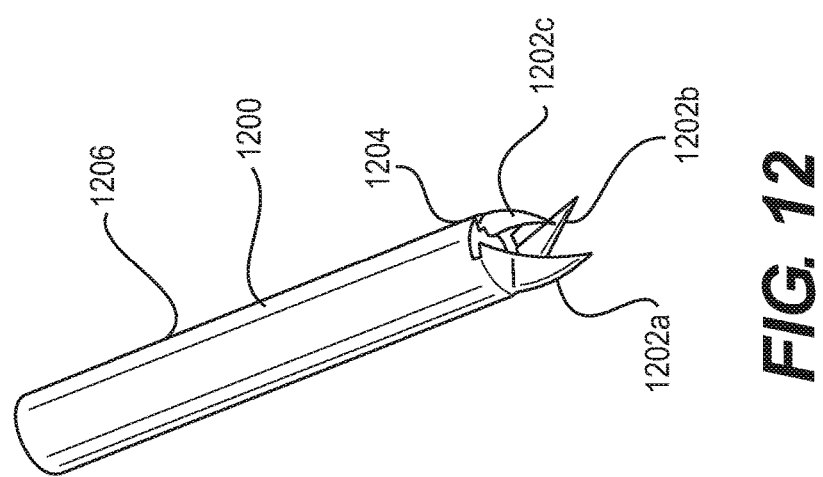
FIG. 12

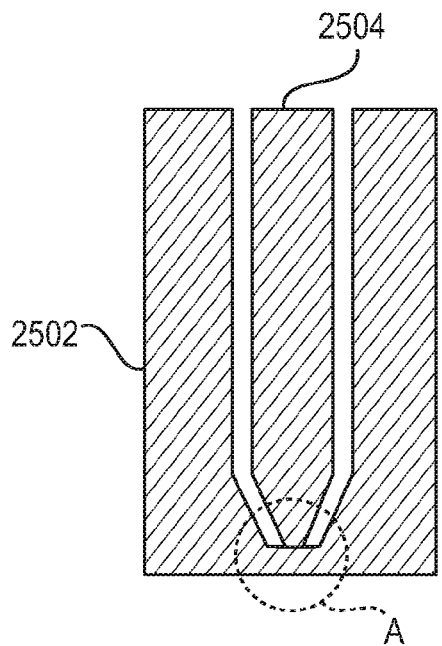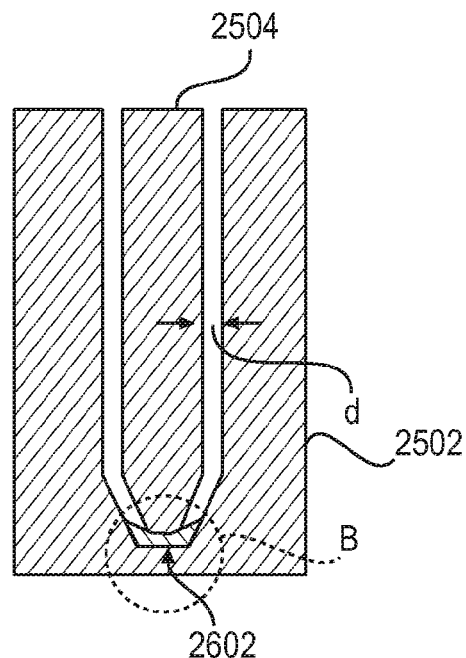
*FIG. 25A*  *FIG. 26A*
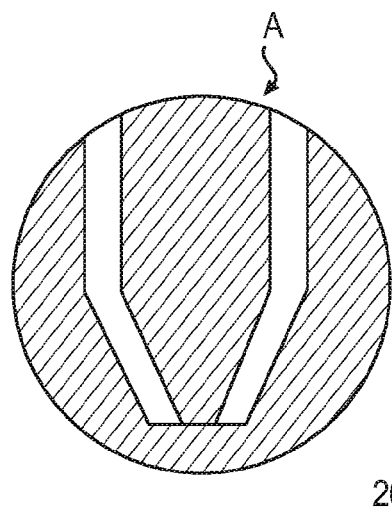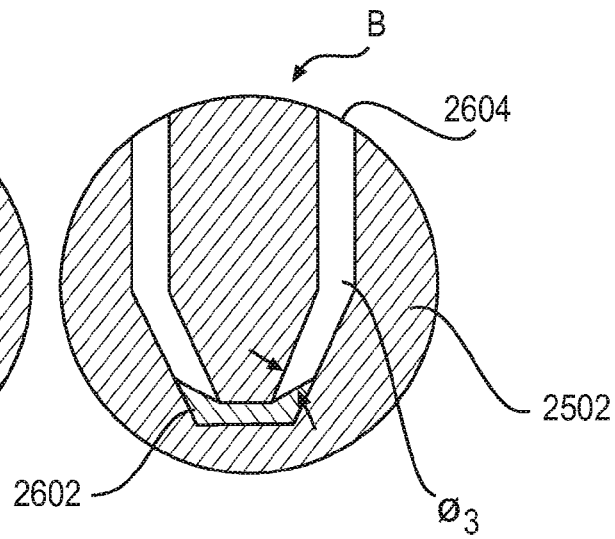
*FIG. 25B*  *FIG. 26B*

APPARATUS AND METHOD FOR ECONOMIC, FAST AND EASY SAMPLING OF FOOD AND ENVIRONMENTAL SAMPLES

CROSS-REFERENCE TO RELATED PATENT APPLICATION

The present patent application claims priority to U.S. Provisional Patent Application No. 62/156,308, filed on May 3, 2015, U.S. Provisional Patent Application No. 62/234,104, filed on Sep. 29, 2015, which is hereby incorporated by reference in its entirety for all purposes.

TECHNICAL FIELD

The embodiments described herein relate generally to sampling of materials and more specifically to solid or substantially solid material sampling for food and environmental sciences, and biological, chemical, medical and related fields.

BACKGROUND

As those of skill in the art can appreciate, an automated pipetting system is generally a device that performs programmed transfers of liquid between preselected groups of containers. Laboratory manuals tools called pipettes, used by lab workers and employed in robotic systems alike, are commonly used in application for molecular biology, analytical chemistry, medical tests, and other fields, to transport a measured volume of liquid. As those of skill in the art can appreciate, while such conventional systems for testing are substantially well developed, they are generally engineered to handle liquid samples and are not particularly well adapted for other materials.

For example, there are other applications that require the capture of solid specimens for archiving, profiling, monitoring, testing, or other purposes. A common example is in the food and environmental sciences, where samples of solid material, such as the intact muscle mass of an animal, is desired to be sampled. Another is in a medical setting, where a biopsy might be desired from a medical sample. With solid samples, the sample texture can vary significantly, such as for example having soft, hard, dry, moist, oily, and/or viscous forms. These and other characteristics create substantial difficulties with known collection systems and apparatus.

In addition to just the physical issues with collection of samples, there are also additional requirements such as turn-around time per sample, convenience of use, or independent sampling events that are important in the context of the hardware solution. As such, the hardware solid sampling solution should be reasonably affordable for the relevant application, relatively easy to assemble and use by skilled persons, and preferably disposable to allow isolated sampling incidents and potentially very short lag-time to process multiple samples back-to-back. Currently, certain biopsy punches are available for solid samples, but most of the foregoing issues are not addressed by such hardware, including the problem that they are not particularly ideal for quick turnaround time applications, lacking good ways of ensuring the captured sample is retained, and not providing an easy manner of releasing the captured samples.

Accordingly, it would be desirable to provide systems, methods, and modes for sampling of solid or substantially solid materials for food, environmental and related sciences, and for the biological, chemical, medical and related fields.

SUMMARY

An object of the embodiments is to substantially solve at least the problems and/or disadvantages discussed above, and to provide at least one or more of the advantages described below.

It is therefore a general aspect of the embodiments to provide systems, methods, and modes for sampling of solid, high viscosity liquids, or substantially solid materials for biological, chemical, medical, and other types of testing with a pipette device that will obviate or minimize problems of the type previously described.

According to a first aspect of the embodiments, a handheld solid sample pipette device is provided comprising a pipette tube, with a plurality of sharpened teeth adapted to pierce the solid, high viscosity liquid, or substantially solid material, further adapted to be matingly attached to a device that comprises a handle, plunger, and a piston within a shell of the device and wherein a spring is positioned to return the plunger to a non-depressed position following depression of the plunger, wherein a sample of the material can be ejected from the handheld device. According to further aspects of the embodiments, the handheld device further comprises a shear ring apparatus that comprises a tube portion, a plurality of shear ring teeth, and a knobbed plate for rotating the shear ring; following insertion of the pipette with sharpened teeth into the solid, high viscosity liquid, or substantially solid sample, the shear ring apparatus is pressed into the sample as well, such that the shear ring tube, which is slidingly engaged about the pipette tube, slides over the pipette tube into the sample. The shear ring teeth pierce the sample, and at a certain point of insertion, the shear ring apparatus is rotated in either or both a clockwise or counter-clockwise direction such that the shear ring teeth severs a portion of the material to be sampled. The severed or sheared off portion then remains within the pipette tube, for removal, and analysis. According to further aspects of the embodiments, the shear ring apparatus and main body portion can be packaged as one assembly, and the user does not have to assemble it before each use. According to further aspects of the embodiments, the handheld solid sample pipette device can be used for sampling muscle tissue, food in both simple (such as fish, steak, vegetables, fruit, beans, among other types) and complex (such as burrito, ravioli, pizza, granola, among many other types) formats, among other solid or high viscosity liquid materials. The samples obtained by handheld solid sample pipette device can be subject to the following types of tests: deoxyribonucleic acids, mass spectrometry, chromatography, among others. According to still further aspects of the embodiments, the amount of sample that can be obtained can range from about 20 to about 200 milligrams, depending on the density of the sample material. However, smaller or larger samples (out of the specified range) can potentially be collected based on certain characteristics of the sample.

BRIEF DESCRIPTION OF THE DRAWINGS

The above and other objects and features of the embodiments will become apparent and more readily appreciated from the following description of the embodiments with reference to the following Figures, wherein like reference numerals refer to like parts throughout the various Figures unless otherwise specified, and wherein:

FIG. 10 illustrates a close-up sectional view of the shear ring portion of the handheld solid sample pipette device of FIG. 4 as it encounters a solid sample according to aspects of the embodiments.

FIG. 11 illustrates a close-up sectional view of the shear ring portion of the handheld solid sample pipette device of FIG. 4 as it penetrates and retrieves a solid sample according to aspects of the embodiments.

FIG. 12 illustrates a perspective view of a portion of a helix shear ring for use with the handheld solid sample pipette device of FIG. 4 according to further aspects of the embodiments.

FIG. 13A illustrates a cross sectional view of a solid sample as it has been cut with the handheld solid sample pipette device of FIG. 4, but without showing the device, according to aspects of the embodiments, and FIG. 13B illustrates the solid sample after it has been removed from the handheld solid sample pipette device of FIG. 4

FIG. 25A illustrates a cross-sectional view of a conventional direct injection molding system that can be used to create a conventional pipette, and FIG. 25B illustrates a close-up cross-sectional view of a tip portion of the direct injection molding system of FIG. 25A.

FIG. 26A illustrates a cross-sectional view of direct injection molding system that can be used to create a sharpened pipette according to aspects of the embodiments, and FIG. 26B illustrates a close-up cross sectional view of a tip portion of the direct injection molding system of FIG. 26A.

DETAILED DESCRIPTION

Figure 1:
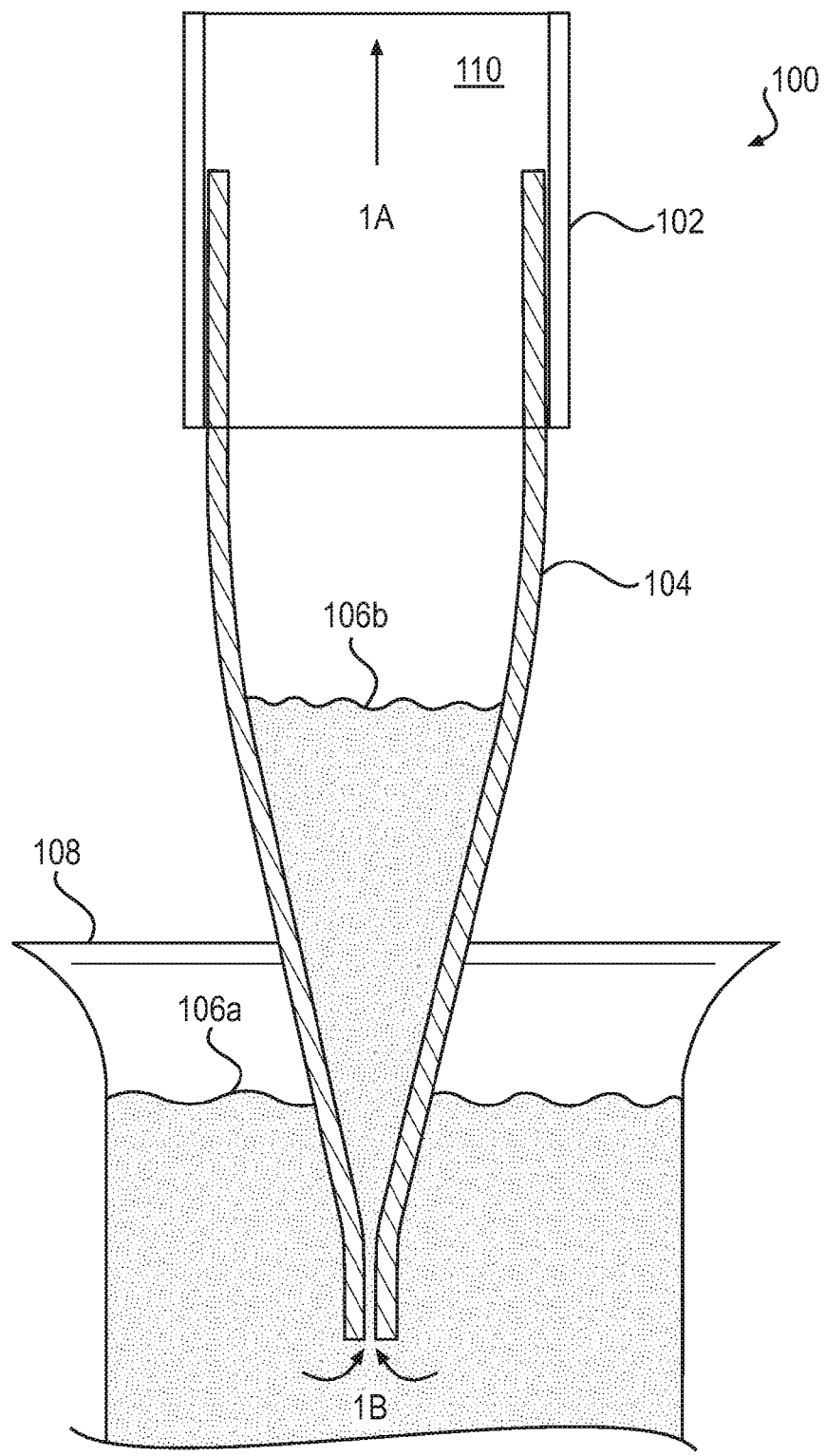
FIG. 1 illustrates an exemplary pipette.

The embodiments are described more fully hereinafter with reference to the accompanying drawings, in which embodiments of the inventive concept are shown. In the drawings, the size and relative sizes of layers and regions may be exaggerated for clarity. Like numbers refer to like elements throughout. The embodiments can, however, be embodied in many different forms and should not be construed as limited to the embodiments set forth herein. Rather, these embodiments are provided so that this disclosure will be thorough and complete, and will fully convey the scope of the inventive concept to those skilled in the art. The scope of the embodiments is therefore defined by the appended claims. The following embodiments are discussed, for simplicity, with regard to the terminology and structure of a handheld solid sample pipette device. However, the embodiments to be discussed next are not limited to these systems but can be applied to other systems, such as automated pipetting systems for sampling solids, high viscosity liquids, or substantially solid samples according to aspects of the embodiments.

Reference throughout the specification to "one embodiment" or "an embodiment" means that a particular feature, structure, or characteristic described in connection with an embodiment is included in at least one embodiment of the embodiments. Thus, the appearance of the phrases "in one embodiment" on "in an embodiment" in various places throughout the specification is not necessarily referring to the same embodiment. Further, the particular feature, structures, or characteristics can be combined in any suitable manner in one or more embodiments.

According to embodiments, the problems described above can be addressed by, for example, a handheld solid sample pipette device according to aspects of the embodiments that can be used to obtain samples of solid or substantially solid materials for chemical, biological, and other testing purposes. The handheld solid sample pipette device comprises a pipette tube, with a plurality of sharpened teeth adapted to pierce the solid or substantially solid material, further adapted to be matingly attached to a device that comprises a handle, plunger, and a piston within a shell of the device and wherein a spring is positioned to return the plunger to a non-depressed position following depression of the plunger, wherein a sample of the material can be ejected from the handheld device.

According to further aspects of the embodiments, the handheld device further comprises a shear ring apparatus that comprises a tube portion, a plurality of shear ring teeth, and a knobbed plate for rotating the shear ring; following insertion of the pipette with sharpened teeth into the solid or substantially solid sample, the shear ring apparatus is pressed into the sample as well, such that the shear ring tube, which is slidingly engaged about the pipette tube, slides over the pipette tube into the sample. The shear ring teeth pierce the sample, and at a certain point of insertion, the shear ring apparatus is rotated in either or both a clockwise or counter-clockwise manner such that the shear ring teeth sever a portion of the material to be sampled such that the portion remains within the pipette tube, for removal, and analysis.

The following is a list of the elements of the Figures in numerical order:
100 Prior Art Liquid Sample Pipette
102 Pipette Holder
104 Pipette Device
106 Liquid Sample
108 Liquid Sample Holder (Beaker)
200 Liquid Handling apparatus
202 Multiple-Pipette Head
204 Pipetting Apparatus
206 Block
302 Pipette Tips
304 Tip Axis
306 Pipette Cones
308 Cavities
310 Cylindrical Insertion Openings
312 Underside
314 Stop
316 Transport Openings
318 Conical Plug-in Openings
318 Conical insertion opening
320 Upper Side
322 Seal
324 Wall
326 Devices
328 Retaining Openings
330 Retaining Axes
400 Handheld Solid Sample Pipette Device (Pipette Device)
402 Plunger
404 Handle
406 Main Tube
408 Pipette
410 Shear Ring Apparatus
502 Spring
504 Core Guide
506 Plunger
508 Piston
510 Sample Insertion Line/Ring
512 Pipette Body
514 Pipette Piercing Tip
702 Solid Sample
703 Sampled Solid
902 Shear Ring Teeth
904 Shear Ring Teeth Channel
906 Shear Ring Body
908 Shear Ring Plate
910 Shear Ring Plate Knobs
1200 Helix Shear Ring
1202 Helix Shear Ring Teeth
1204 Helix Shear Ring Teeth Channel
1206 Helix Shear Ring Body
1302 First Channel
1304 Second Channel
1400 Method of Use of Pipette Device 400
1402-1410 Method Steps of Method 1400
1900 Sharpened Pipette Tube
2100 Pipette Sharpening Apparatus
2102 Mount Motor
2104 Mounting Spindle
2106 Unsharpened Pipette Tube (Unsharpened Pipette)
2202 Mounting Spindle First Surface
2302 Grinding Surface
2304a First Pipette Tip Sample Contact Surface
2304b Second Pipette Tip Sample Contact Surface
2402 Second Sharpened Pipette Tube (Second Sharpened Pipette)
2500 First Direct Injection Molding System (First Molding System)
2600 Second Direct Injection Molding System (Second Molding System)
2602 Second Molding System Outer Mold (Outer Mold)
2604 Second Molding System Inner Mold (Inner Mold)
2606 Second Molding System Insert (Insert)
2700 Third Direct Injection Molding System (Third Molding System)
2800 First Conventional Biopsy Punch
2802 Conventional Biopsy Punch
2804 Plunger
2900 Positive Displacement Pipette System
2902 Piston
3000 Hybrid Positive Displacement Pipette-Biopsy Punch System The word "pipetting" refers to a laboratory manual tool called a pipette, as shown in FIG. 1, which is the commonly used in molecular biology, analytical chemistry, and medical tests, among numerous other fields, to transport a measured volume. Moreover its performances may be regulated by the International Standard ISO8655-1:2002.

Figure 2:
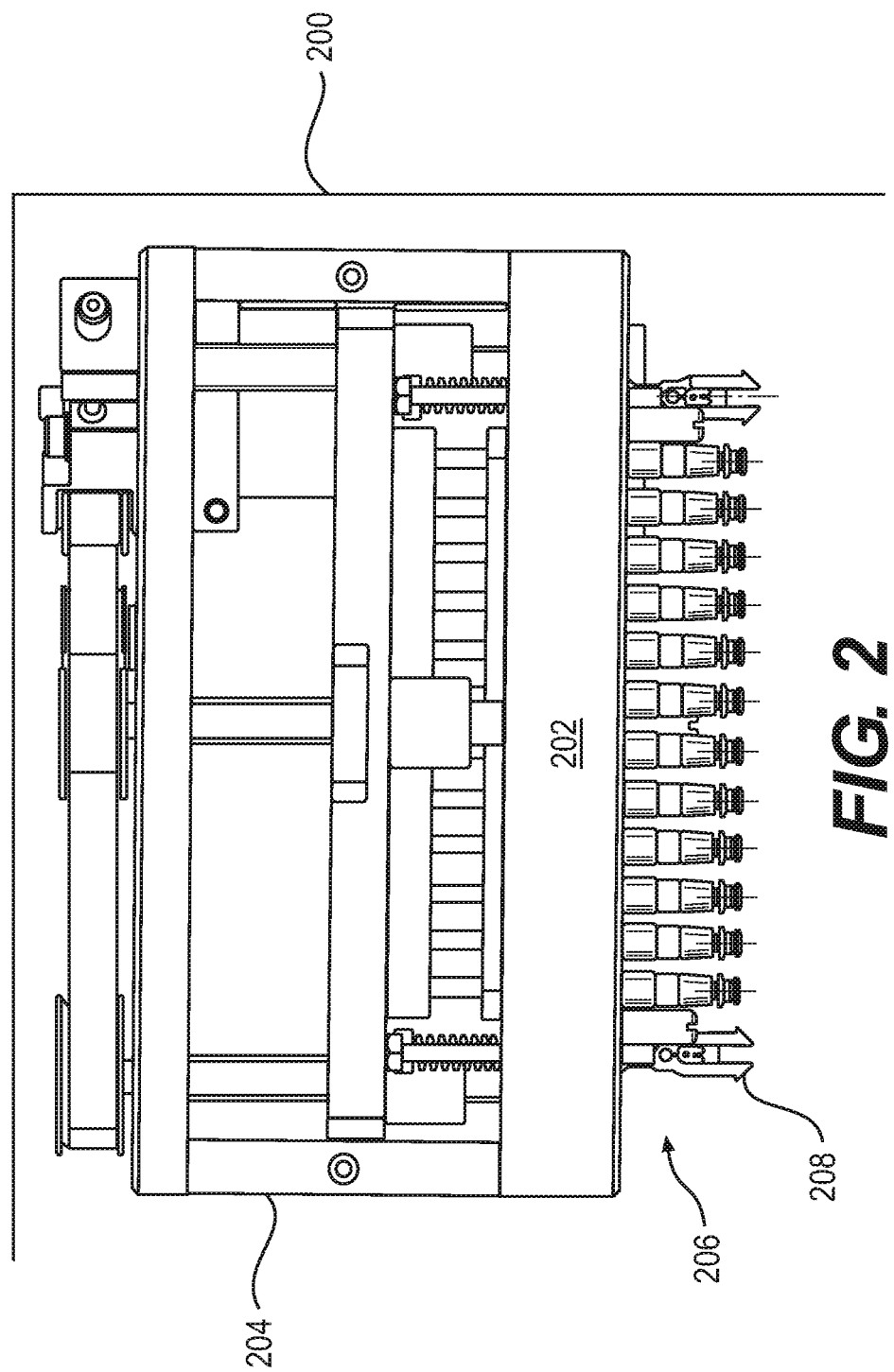
FIG. 2 illustrates an exemplary multiple pipette head for use in a material handling apparatus.
Figure 3:
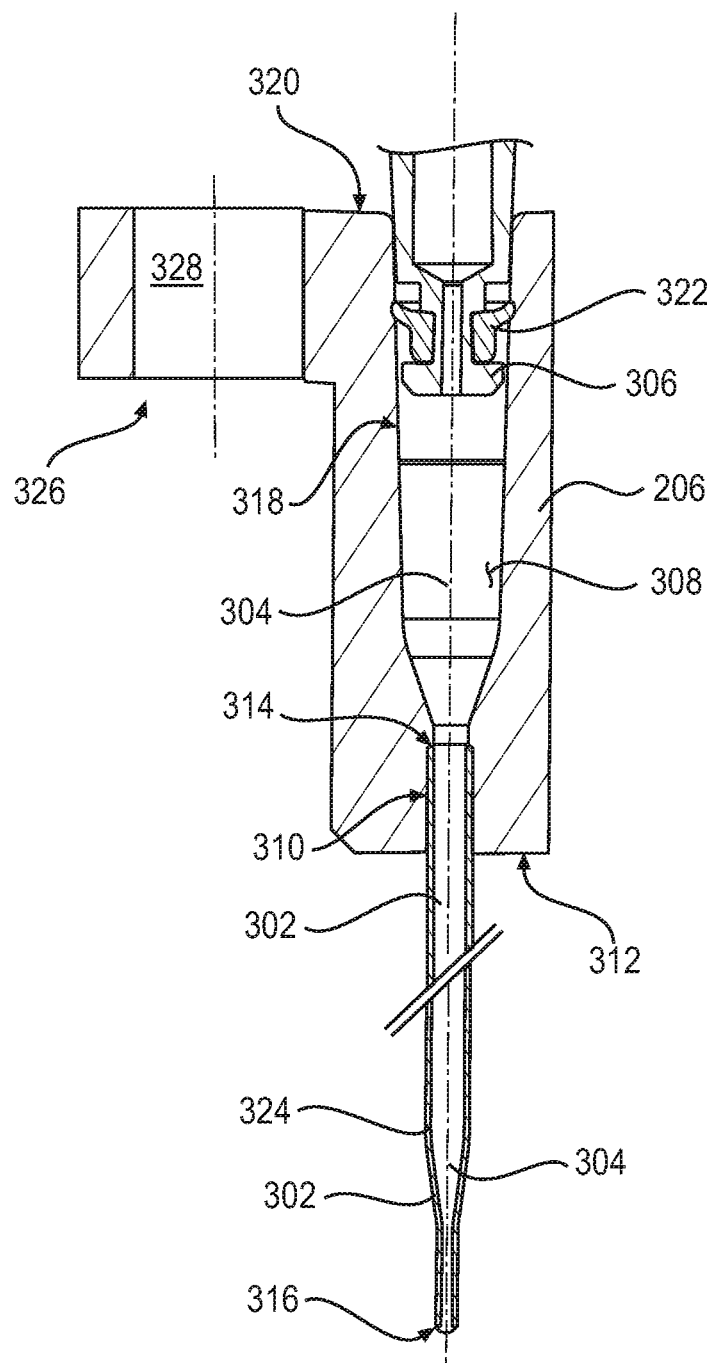
FIG. 3 illustrates a vertical partial section through a block for holding a plurality of pipettes.

Referring to FIG. 1, which illustrates conventional pipette 104, holder 102 acts as an interface between pipette 104 and the balance of the automated pipetting system shown and discussed in reference to FIGS. 2 and 3. Pipette 104 may be inserted into a sample 106, and a suction can be applied in the direction of arrow 1A such that air 110 is evacuated from holder 102 and pipette 104, drawing sample 106a from holder 108 into pipette 104 in the direction of arrow 1B as sample 106b. If the suction is maintained, pipette 104 can be moved to put sample 106b into a different container that can store it, or contains another chemical for further processing.

In exemplary embodiments, automated pipetting systems, also known as handling robots, are employed. As those of skill in the art can appreciate, the latter definition is preferred whenever add-on modules are present (e.g., laboratory shaker), while the former typically focuses on material transfer property. One of main advantages of these devices is the ability to enhance the reproducibility and the throughput of laboratory experiments.

One component of the exemplary automated system is a pipetting head. In certain embodiments, the pipetting heads are based on a peristaltic pump system, while some anthropomorphic systems directly use manual pipettes. Pipetting heads can be multi-channel or single-channel: while the former has higher throughput, the latter has greater flexibility and reproducibility. For an accurate placement into the source and destination containers, the pipetting head is placed on an automated axis system, based on servo motors, stepper motors or any analogous system.

In exemplary embodiments the automated systems include a user interface. The user interface allows communication between the user and the system via a personal computer or touchscreen. More advanced user interfaces employed herein provide the possibility for user to design their own experiments to be executed on the system.

In exemplary embodiments, the automated pipetting systems may obtain a volume or amount of material from a source by creating suction, described as aspirating, and dispensing this material over the destination container. This may be achieved by the pipetting head installed on the system.

In exemplary embodiments, the materials are not in direct contact with the pipetting head, but are held by pipette tips 104. Pipette tips 104 can be a permanent structure, or disposable conical pieces. Pipette tips 104 can be made from injection molded plastic, which material may be polypropylene or any other suitable material, and may have the advantage of being so inexpensive that they are discarded between material transfers, thus substantially if not completely removing any chance of cross contamination. As those of skill in the art can appreciate, the choice of the most suitable tip depends at least in part on the dispensing volume set on the pipetting head.

Attention is now directed to FIGS. 2 and 3, which illustrate system and component views of an exemplary automated sample pipetting system.

FIG. 2 illustrates a view of an exemplary multiple-pipette head 202 of a handling apparatus 200. Such handling apparatus 200 comprises a pipetting apparatus 204. The pipetting apparatus 204 comprises a block 206 for holding a plurality of identically configured pipette tips 302 having a tip axis 304 and for connecting these pipette tips 302 to a plurality of pipette cones 306 of a multiple-pipette head 202 of this handling apparatus 200.

FIG. 3 illustrates a vertical partial section through an exemplary block 206 for holding identically configured pipette tips 302. Block 206 comprises a plurality of cavities 308 penetrating the block 206 that, in this exemplary case, are disposed parallel in an array that corresponds to the arrangement of wells of a standard microplate. A microplate, as known to those of skill in the art, is a flat plate with multiple "wells" used as small test tubes. The microplate may be used as a tool in analytical research and clinical diagnostic testing in accordance with certain embodiments.

Block 206 additionally comprises a plurality of cylindrical insertion openings 310 disposed on an underside 312 of block 206 and forming a lower opening of the cavities 308. These insertion openings 310 are configured for the frictional receipt of respectively one pipette tip 302 in such a manner that the tip axes 304 of all the inserted pipette tips 302 are disposed substantially parallel to one another in this array. At the same time, in this case, each insertion opening 310 has a stop 314 that is configured for being acted upon by a rear end of an inserted pipette tip 302. The positive action of the stop 314 in the cylindrical insertion opening 310 ensures that the transport openings 316 of the pipette tips 302, which all have precisely the same length within the dimensional accuracy of the manufacturing process, lie in one plane. Thus, an exact height position of the transport openings 316 of all the pipette tips 302 can be set with a handling robot (not shown) of the handling apparatus 200 during the pipetting (in particular during the aspirating) of materials. Unlike the insertion just described, pipette tips 302 that all have precisely the same length can be lowered frictionally with the aid of a gauge in a cylindrical insertion opening 310 which has no stop 314.

Block 206 further comprises a plurality of conical plug-in openings 318 disposed on an upper side 320 of the block and forming an upper opening of the cavities 308. Each of these conical plug-in openings 318 is configured for the sealing introduction of a pipette cone 306 of a multiple-pipette head 202. Pipette cone 306 typically comprises a seal 322 that abuts sealingly against a conical insertion opening 318 such as in an elastically deformed manner.

The exemplary pipetting apparatus 204 additionally comprises a number of tubular pipette tips 302 each having a wall 324 extending along the tip axis 4 and having a transport opening 316 disposed at a front end for receiving (aspirating) and delivering (dispensing) samples. Such a pipetting apparatus 204 also comprises devices 326 for connecting block 206 and multiple-pipette head 202. An exemplary device 326 is shown in FIGS. 2 and 3. Device 326 comprises retaining openings 328 with retaining axes 330 for receiving retaining devices 208 fastened to the multiple-pipette head 202.

In certain exemplary embodiments, additional features are implemented for the capture of solid specimens, such as for archiving, profiling, monitoring, testing, or other purposes. The benefits of these embodiments are useful in many disciplines, sciences and fields. Exemplary areas include the food and environmental sciences field, where samples of solid material, such as the intact muscle mass of an animal, or tissue from a plant, is desired to be sampled. Another area is in medical setting, wherein the biopsy requires extraction of cells from organs of the patient. Another use case is in an environmental setting, wherein the texture of different samples could vary significantly.

Figure 4:
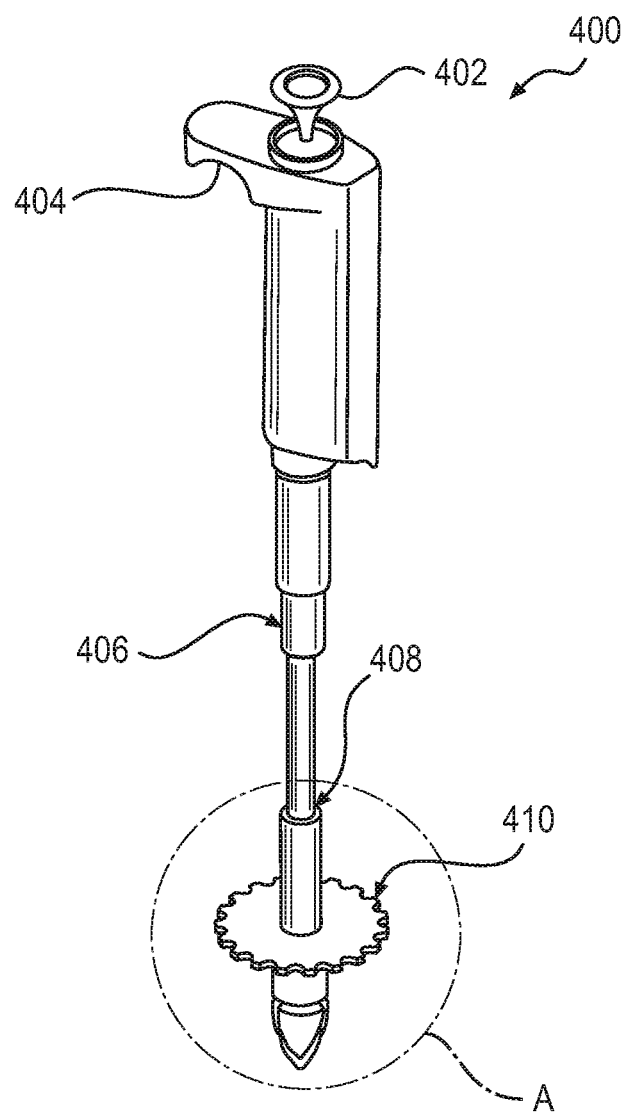
FIG. 4 illustrates a perspective view of an exemplary handheld solid sample pipette device according to certain aspects of the embodiments.

FIG. 4 illustrates a perspective view of an exemplary handheld solid sample pipette device (pipette tip device) 400 according to certain aspects of the embodiments. Pipette device 400 comprises, among other components, plunger 402, handle 404, main tube 406, pipette 408, and shear ring apparatus 410. In operation, and as described in greater detail below, pipette device 400 according to aspects of the embodiments can be used to sample solids, high viscosity liquids, or substantially solid materials that ordinary liquid-based pipettes would not be able to sample.

A lower portion of pipette device 400 can be inserted into the material, and shear ring apparatus 410 can then be rotated to sever the sample portion away from the remainder of the material, encasing the sample portion within a lower portion of pipette 408. Pipette device 400 is then removed from the material to be sampled, held over a sample receptacle, and plunger 402 is depressed, which forces a piston down in direct contact with the sample such that the sample portion is then ejected into the sample receptacle. An internally located spring, not visible in FIG. 4, returns plunger 402 to its non-depressed condition, and pipette device 400 can be used again, following cleaning and sterilization, if such sample and the testing thereof permit, or it can be disposed of properly at that point.

A detailed discussion of these and other components of pipette device 400, as well as further aspects of the embodiments, will now be discussed in regard to FIGS. 5, 6, 7, 8, 9A, 9B, 10, 11, 12, and 13. The elements of these figures, including pipette device 400, can be used in accompaniment and correspondence with any other aspects and embodiments disclosed herein.

Figure 5:
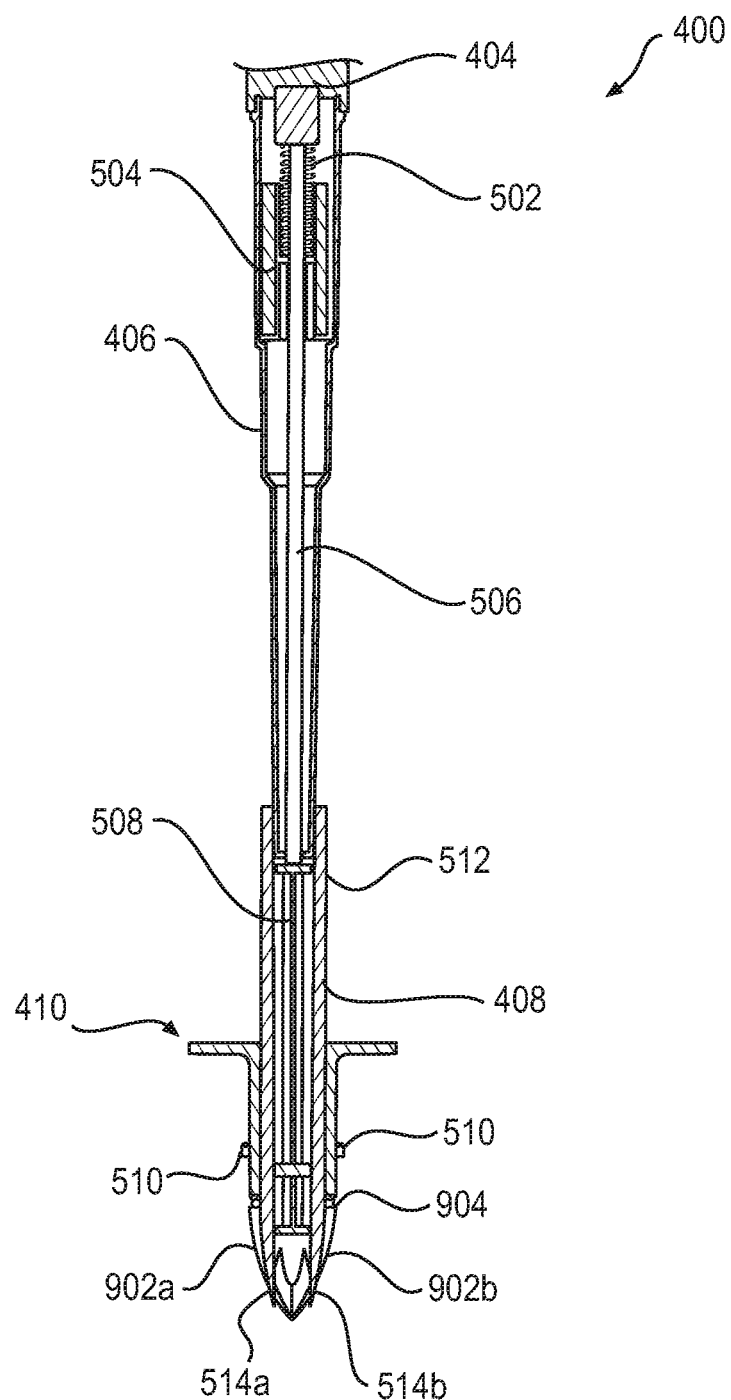
FIG. 5 illustrates a cross-sectional view of the handheld solid sample pipette device of FIG. 4 according to certain aspects of the embodiments.
Figure 6:
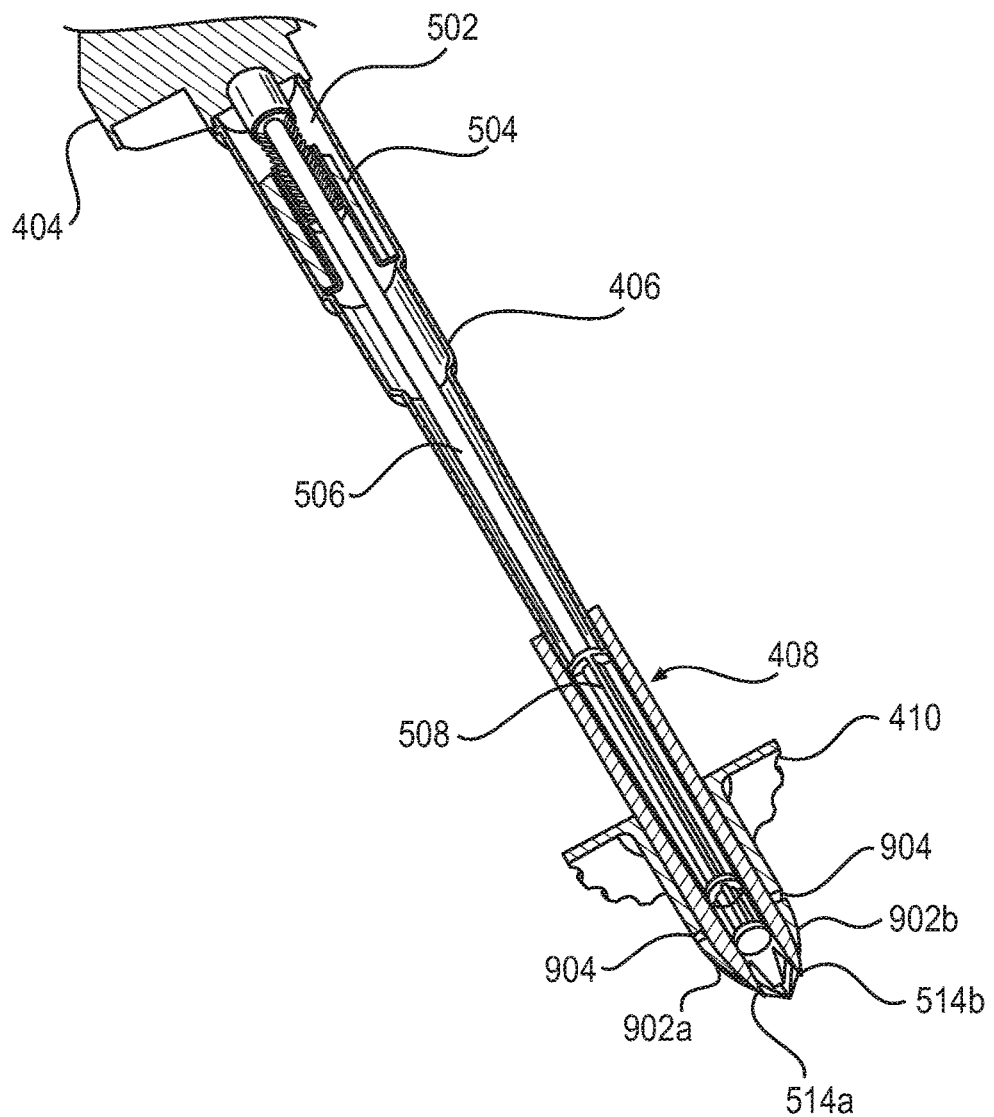
FIG. 6 illustrates a perspective cross-sectional view of the handheld solid sample pipette device of FIG. 4 according to certain aspects of the embodiments.
Figure 8:
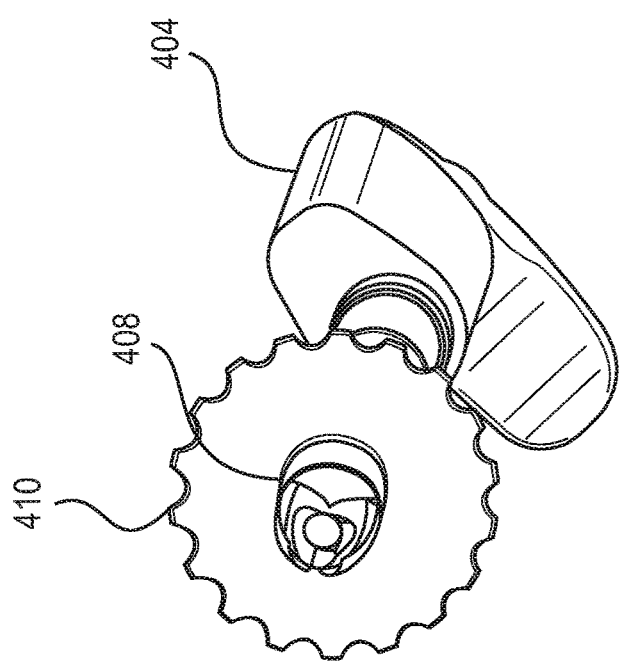
FIG. 8 illustrates a close up bottom perspective view of the shear ring portion of the handheld solid sample pipette device of FIG. 4 according to certain aspects of the embodiments.
Figure 9B:
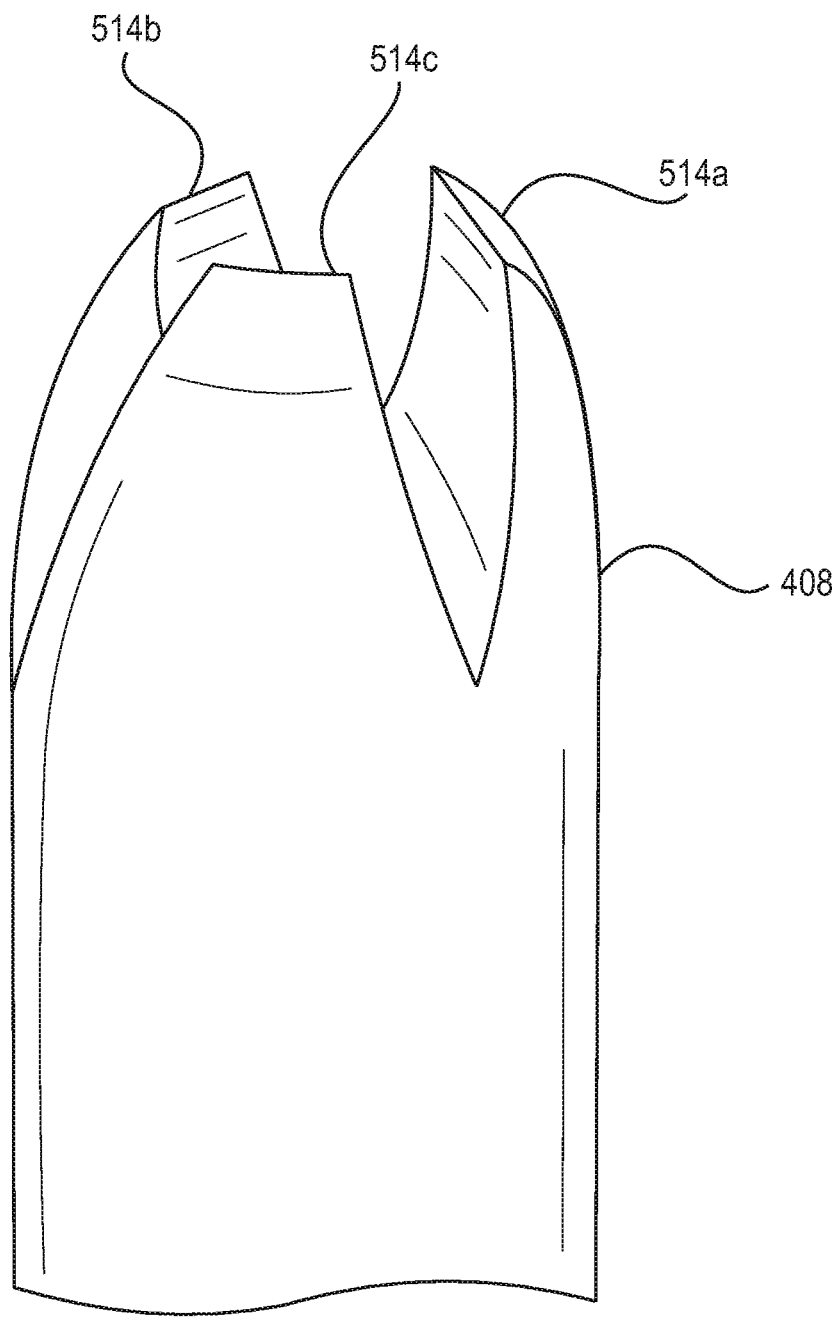
FIG. 9B illustrates a close-up perspective view of the pipette according to aspects of the embodiments.

FIGS. 5, 6 and 8, which illustrate differing views of the pipette device 400 of FIG. 4, are next described. In particular, FIG. 5 illustrates a cross-sectional view of pipette device 400 of FIG. 4, FIG. 6 illustrates a perspective cross-sectional view of pipette device 400, and FIG. 8 illustrates a close up bottom perspective view of a shear ring portion of pipette device 400, according to aspects of the embodiments.

Referring now to FIGS. 5, 6, and 8, pipette device 400 can be seen to include handle 404. Handle 404 provides the operator with a solid mechanism by which to grab and hold onto pipette device 400 when inserting it into a sample material and when retracting it. Located on top of handle 404 is plunger 402 (shown more clearly in FIG. 4) and which extends through handle 404. Plunger 402 is retained in a non-depressed position by spring 502 in a manner known to those of skill in the art, and is contained by core guide 504 to provide for a substantially easy and reciprocating motion with respect to main tube 406 of pipette device 400 according to aspects of the embodiments (which can be especially seen in regard to FIG. 6). Located at the bottom-most portion of plunger 402 is piston 508. Plunger 402 pushes directly on piston 508 when a sample has been retracted within pipette 408, as described in greater detail below, to eject the sample.

Pipette 408 is fashioned in such a manner, and of such a material that it can be slidingly engaged with main tube 406 of pipette device 400; that is, pipette 408 has an inner diameter that is substantially similar to the outer diameter of main tube 406 so that it frictionally engages with the outer surface of main tube 406; according to further aspects of the embodiments, other retention mechanisms can be used to mate the two components together in such a manner that the two can be mated, but also un-mated at a desired time and location. For example, pipette 408 can screw onto main tube 406, or can snap fit, or can be retained by a retaining ring, or other such similar mechanism as known to those of skill in the art.

Figure 9A:
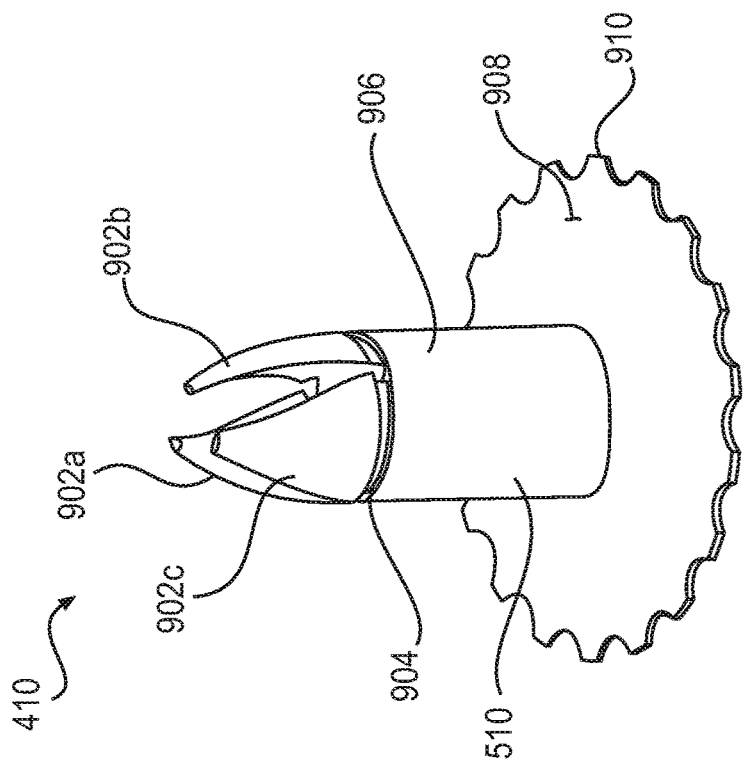
FIG. 9A illustrates a close-up perspective view of the exemplary shear ring according to aspects of the embodiments.

Pipette device 400 further comprises shear ring apparatus 410, a detailed discussion of which is made in regard to FIG. 9A. However, as can be seen in FIGS. 5, 6 and 8, shear ring apparatus 410 comprises sample insertion line/ring 510, which can be used as an alternate means for indicating to the operator when a sufficient depth has been reached of insertion of pipette device 400 into a sample. Alternatively, shear ring teeth channels 904 (described in greater detail in regard to FIG. 9A) can be used as an indication of a sufficient depth of insertion of pipette device 400 into a sample. Located at a bottom most portion of shear ring apparatus 410 are shear ring teeth 902a, 902b and 902c (not shown); operation of shear ring teeth 902a-c is described in greater detail in regard to FIG. 9A. At a bottom-most portion of pipette 408 are pipette piercing tips 514a, 514b which are adapted to pierce the sample when pipette device 400 is inserted therein. These are shown in greater detail in FIG. 9B. As FIGS. 5, 6, and 8 illustrate, shear ring apparatus 410 can also be fabricated in such a manner, and of such a material, such that it too can slidingly engage with an outer surface of pipette 408.

Figure 7:
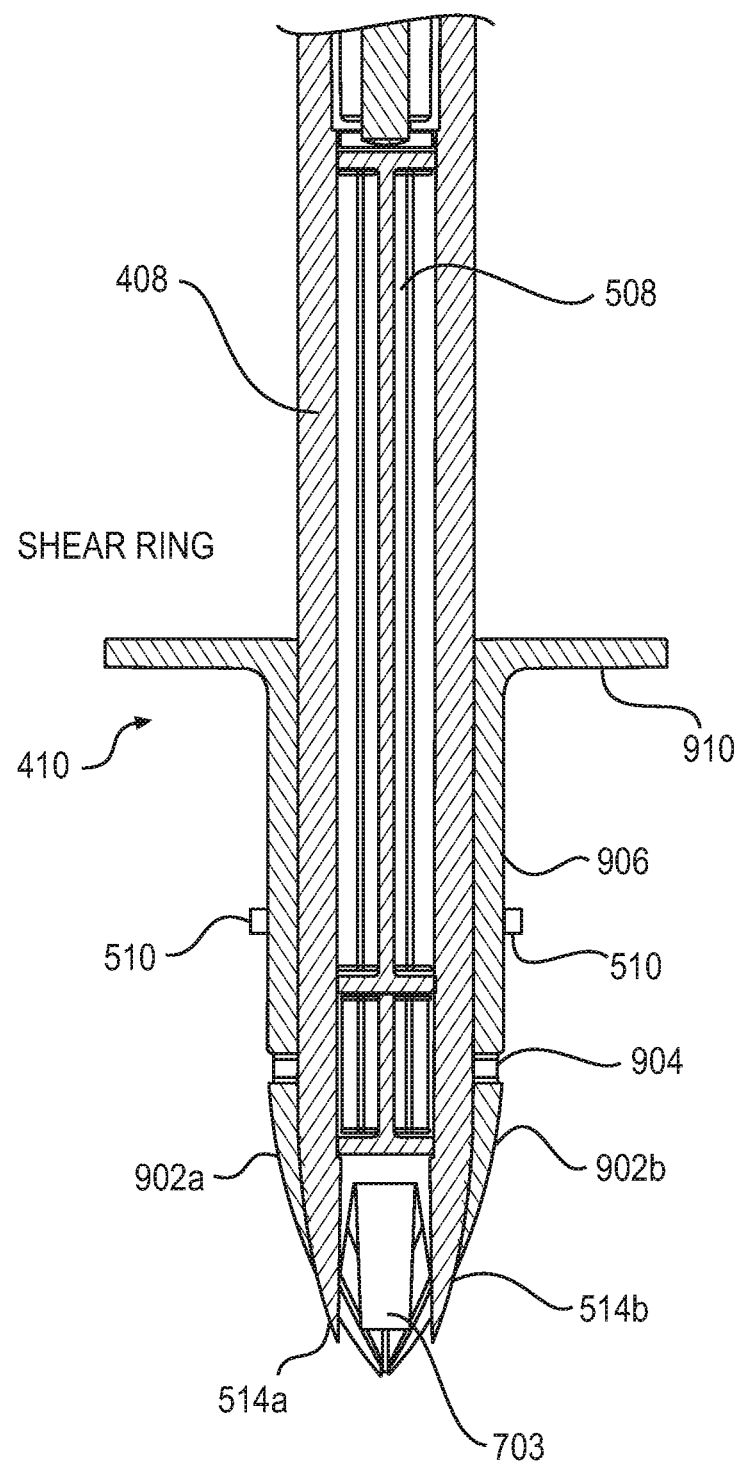
FIG. 7 illustrates a close-up cross-sectional view of a shear ring portion of the handheld solid sample pipette device of FIG. 4 according to certain aspects of the embodiments.

FIGS. 7 and 9A are next described in accordance with certain embodiments. In particular, FIG. 7 illustrates a close-up cross-sectional view of a bottom portion of pipette device 400 of FIG. 4, including shear ring apparatus 410, while FIG. 9A illustrates a close-up perspective view of shear ring 410 of pipette device 400, according to aspects of the embodiments.

Referring first to FIG. 7, a bottom-most portion of pipette device 400 is shown that includes shear ring apparatus 410, a portion of pipette 408, piston 508, and sampled solid 703. The state of pipette device 400 in FIG. 7 is one in which it has been inserted into sample 703, shear ring 410 has been engaged to cut-off or shear a portion of a sample 702 (shown in FIG. 10) to provide sampled solid 703, and piston 508 is being lowered through operation of plunger 402 to engage with and push out sampled solid 703 from inside pipette 508.

In FIG. 7, it can be seen that shear ring apparatus 410 includes a plurality of shear ring teeth 902a, 902b (shown and discussed in greater detail in FIG. 9A), and shear ring teeth channel 904, as well as sample insertion line/ring 510. Shear ring teeth 902a,b are in a state wherein they have pierced sample 702, and shear ring apparatus 410 has been pushed to the point where shear ring teeth 902a,b have become co-located with pipette piercing tips 514a, 514b. Shear ring apparatus 410 is next rotated, either clockwise or counter-clockwise, to cause shear ring teeth 902a-c to cut or shear off solid sample 702 to form sampled solid 703. Next, pipette device 410 is extracted from sample 702 and is (normally) positioned above a container to hold sampled solid 703 following ejection thereof.

Figure 15:
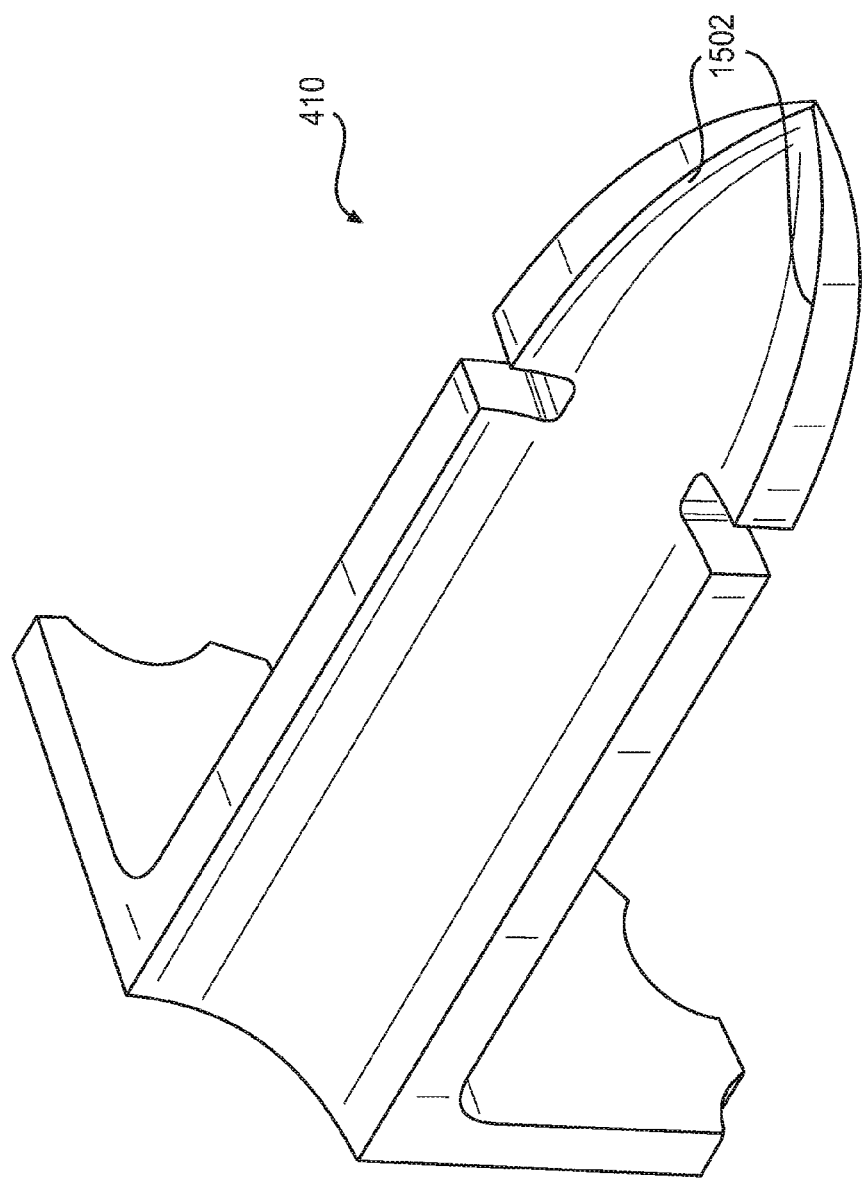
FIG. 15 illustrates a further view of the shear ring of FIG. 9A according to aspects of the embodiments.

The structure and operation of shear ring apparatus 410 will now be described in greater detail in regard to FIG. 9A. In FIG. 9A, shear ring apparatus 410 is shown with shear ring plate 908 resting on a surface, and knobs 910 can be clearly seen; knobs 910 provide a means for an operator to securely grip shear ring apparatus 410 and rotate it either in a clockwise or counter-clockwise direction. In the embodiment of shear ring apparatus 410 shown in FIG. 9A there are three shear ring teeth 902a-c; each is substantially curved and conical in shape, and comprises a formed "sharpened" edge on both sides of shear ring teeth 902; such a sharpened edge can be formed during the manufacturing process, which in the exemplary embodiment an injection molding process. In these are related manufacturing processes, the edge geometry of teeth 902 are be altered for different materials that are to be sampled according to further aspects of the embodiments. According to an aspect of the embodiments, such edge geometry can include an angle of about 0° to about 45°. A further view of shear ring apparatus 410 is shown in FIG. 15.

Further shown in FIG. 9A (and other figures herein) is shear ring teeth channel 904; channel 904 serves at least two purposes. The first is to provide a bending location for each of teeth 902a-c; that is, when shear ring apparatus 410 is engaged about pipette 408, it is of such dimension that the inner diameter of shear ring apparatus 410 is substantially similar to the outer diameter of pipette 408. Teeth 902a-c, because of channel 904, will have a tendency during operation to curve inwards, and "hug" the body of pipette 408, and form a "clamshell" type of configuration prior to being placed about pipette 408. When shear ring apparatus 410 is then inserted into sample 702 following insertion of pipette 408, the plurality of teeth 902a-c will be forced to maintain that close contact, essentially forming a conical shell about pipette tips 514. When shear ring apparatus 410 is then rotated (clockwise, or counter-clockwise, or both), channel 904 assists teeth 902a-c in collapsing more about tips 514, providing a more thorough and efficient means of cutting or shearing the sample 702 such that a separated portion, sampled solid 703, resides in an interior portion of pipette 408. When the pipette assembly is removed from the sample 702, sampled solid 703 remains within pipette 408, until acted upon by plunger 506 and piston 508.

At least on other use of channel 904 is to provide a visual guide as to the proper depth of insertion of pipette 408 into sample 702; as described above, sample insertion line or ring 510 can also perform a similar function.

FIGS. 10 and 11 illustrate the action of insertion and rotation of shear ring apparatus 410 according to certain aspects of the embodiments. As shown in FIG. 10, pipette device 400 has been lowered and is being inserted into sample 702, in the direction of arrow 10A. Tips 514 have pierced sample 702 and are forcing their way into sample 702. According to aspects of the embodiments, therefore, the material that pipette 408 is made of needs to be of sufficient rigidity to withstand the forces required to enter sample 702.

The types of material that may be sampled by pipette device 400 will be plants, vegetables, fruits, and tissue, though the type of material is in no way limited to the foregoing. Thus, for example, a typically hard substance would be granola, tablets, caplets, vegetable such as a radish, or potato, or fruit, such as an apple or pineapple. Any type of meat would require substantial force to pierce and obtain a sample as well, as such materials include relatively long collagen strings that can be tough and difficult to cut or tear. In addition, in exemplary embodiments pipette 408 is manufactured affordably; thus, while an aluminum or other metallic pipette 408 (and any other known materials) is certainly within the scope of the embodiments, such material may be prohibitively costly to manufacture, to use on a wide-scale implementation.

According to certain aspects of the embodiments, a first type of material used solely or in combination for pipette 408 is polycarbonate, while a second type of material used solely or in combination for shear ring apparatus 410 is polypropylene. According to certain aspects of the embodiments, other materials that can be used for the first material to make up pipette 408 with substantially similar characteristics include polycarbonate, medical grade acrylics, PEEK, or Polysulphone. It should be understood by those of skill in the art that such a list is just representative, and is by no means complete, nor is it intended to be construed as such. According to an aspect of the embodiments, other materials that can be used for the above second material to make up shear ring apparatus 410 with substantially similar characteristics include Polypropylene, Polyethylene, Polyethylene Copolymer, Vinyl Acetates (EVA Copolymers), PVCs. It will be understood by those of skill in the art that such a list is just representative, and is by no means complete, nor is it intended to be construed as such.

In FIG. 11, pipette device 400 has been inserted into sample 702 to the position indicated by channel 904. Here, shear ring teeth 902a-c form their clamshell configuration about tips 514; this can be seen in at least FIGS. 5, 6, 7, and 8. At this point, the operator twists shear ring apparatus 410 in the direction of arrows 11A or 11B, or both, to cause the "clamshell" of teeth 902 to cut or shear sample 702. According to certain aspects of the embodiments, with three teeth 902a-c, the twisting motion should encompass about 120° so that the bottom-most portion of teeth 902 travels in an arc long enough to make a complete cut of sample 702.

According to further aspects of the embodiments, shear ring apparatus can include four teeth 902 such that a complete cutting motion occurs in a rotation of about 45°; of course, there is a practical limit of manufacturing as to how many teeth 902 can be included in shear ring apparatus 410, or of that of pipette tips 514, but any number of teeth 902 and/or tips 514 are considered to be within the aspects of the embodiments.

Figure 16:
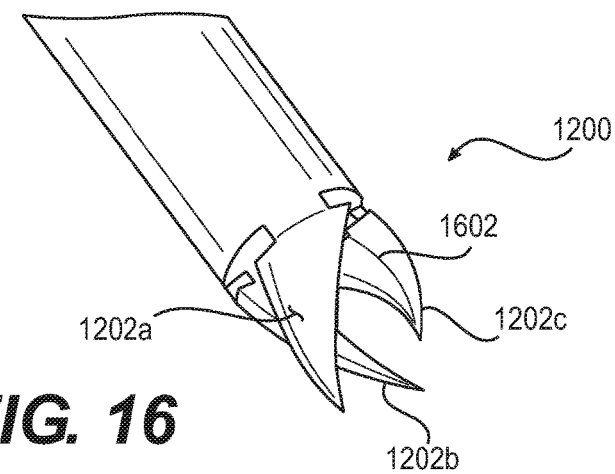
FIGS. 16, 17A, 17B and 18 illustrate further views of the helix shear ring of FIG. 12 according to aspects of the embodiments.
Figure 17A:
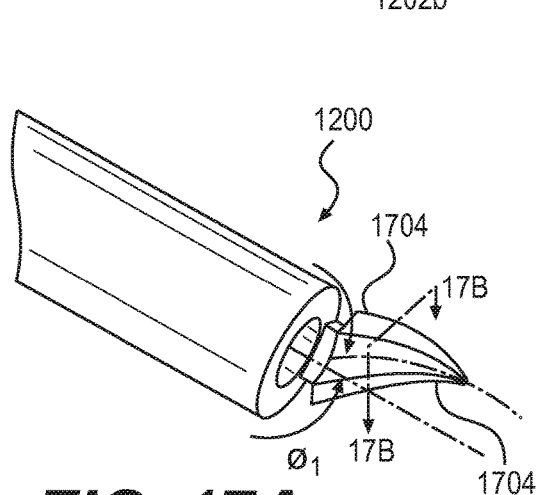
Figure 17B:
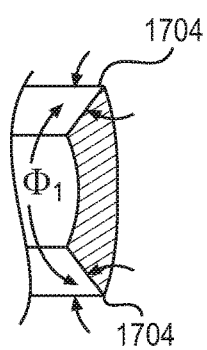
Figure 18:
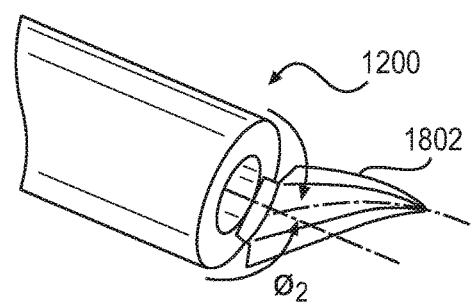

FIG. 12 illustrates a perspective view of a portion of helix shear ring 1200 for use with pipette device 400 of FIG. 4 according to further aspects of the embodiments. The portions of helix shear ring 1200 not shown are substantially similar to those of shear ring 400; therefore, a detailed discussion thereof has been omitted in fulfillment of the dual purposes of clarity and brevity. Further views of helix shear ring 1200 are shown in FIGS. 16, 17, and 18.

Helix shear ring 1200 comprises teeth 1202a, 1202b, 1202c and 1202c, channel 1204 and body 1206. Channel 1204 operates in a substantially similar manner as channel 904, and therefore a detailed discussion thereof can be omitted in fulfillment of the dual purposes of clarity and brevity. Teeth 1202a-c are formed such that lines that represent a centrally located axis in each tooth would form a helix shape, i.e., they twist about each other. Thus, each central axis of teeth 1202a-c are located about 120° apart from each other.

According to further aspects of the embodiments, however, each central axis, i.e., the teeth, can be formed at different angles that are non-zero. That is, if each central axis departs from a base at a very small twisting angle, the helix formed will be very long; if the angle the central axes form is substantial, then the teeth 902 will be of greater twist, and the apparent helix shape would be much more pronounced. By forming teeth 1202 in this manner, and providing edge geometry as described above that has an angle to form a blade on the teeth's edges, a substantially improved cutting or shearing action can occur, one which is more thorough, and efficient, and therefore requires less force.

According to certain aspects of the embodiments, helix teeth 1202 are formed such that no additional twisting is necessary; as the helical cutting teeth 1202 are inserted into sample 702, they not only cut or shear sample 702, but would also, because of the geometry of the teeth and cutting edge, collapse upon themselves in a closing configuration making a more thorough cut or shear of sample 702. Such functionality can provide the benefit of being able to use softer materials to form helix shear ring 1200, which can be easier to manufacture and/or cost less, or allow helix shear ring 1200 to be used with material or samples 702 that are more difficult to sample.

FIGS. 13A and 13B illustrate the effect of use of shear ring apparatus 410 on sample 702. Beginning with FIG. 13A, first channel 1302 is formed as pipette 408 and inserted into sample 702; first channel 1302 is then slightly enlarged when shear ring apparatus 410 is inserted or pushed down into sample 702 shortly thereafter. After the twisting or shearing action created by rotating shear ring apparatus 410, second channel 1304 is formed as shown in FIG. 13A, thereby forming a separation of sampled solid 703 from sample 702.

FIG. 13B illustrates how sampled solid 703 could appear once it has been retracted from sample 702 and expelled from pipette device 400 according to aspects of the embodiments. The length l of sampled solid 703 substantially matches the depth of insertion of pipette 408, which can be up to the line formed by channel 904, or sample insertion line/ring 510, according to further aspects of the embodiments.

Figure 14:
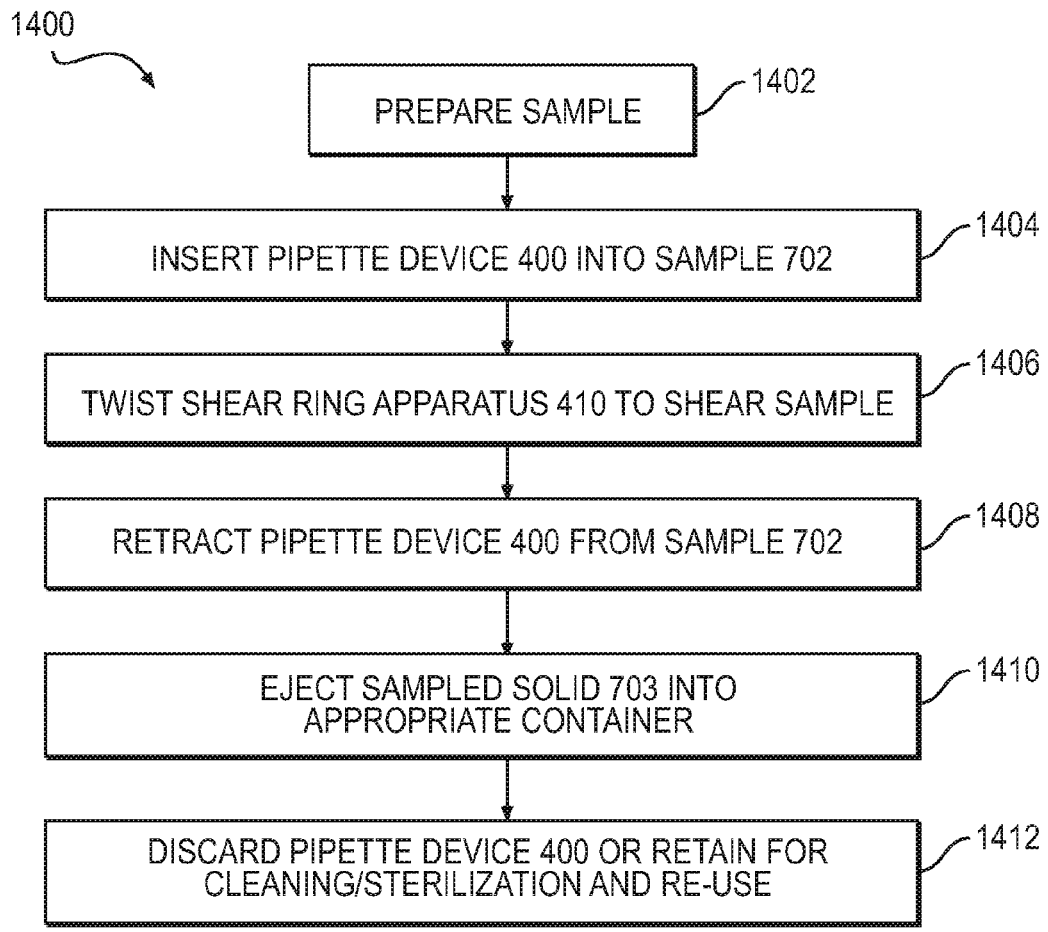
FIG. 14 illustrates a method for use of the handheld solid sample pipette device of FIG. 4 according to aspects of the embodiments.

FIG. 14 illustrates an exemplary method 1400 for use of pipette device 400 of FIG. 4 according to certain aspects of the embodiments. Method 1400 begins with step 1402 wherein sample 702 is prepared for use with pipette device 400. Such preparation can include washing, immersion into liquids or gases, heating, cooling, pressurizing, among other preparation steps. In an automated system, briefly described below, such preparation can include insertion into a device or apparatus that can accommodate numerous samples for use with pipette device 400.

Following preparation in step 1402, method 1400 proceeds to step 1404 wherein pipette device 400 is inserted into sample 702 in a manner as described in greater detail above. According to further aspects of the embodiments, different shear ring apparatus 410 can be used for different types of samples 702, and they can be color coded, or marked in some other manner known to those of skill in the art to differentiate their usage.

In method step 1406, shear ring apparatus 410, having been inserted to the correction position or depth within sample 702, is twisted, as described above, in either or both of a clockwise or counter-clockwise direction a predetermined angle of rotation. According to further aspects of the embodiments, if there are three teeth 902a-c, then such angle of rotation would be about 120° (and could include a few more degrees to ensure separation, as those of skill in the art can appreciate), or if there are four teeth 902a-d, then such angle of rotation would be about 45°, again with a bit more to ensure separation.

Following rotation and shearing of sample 702, pipette device 400 is retracted from the sample (method step 1408), and sampled solid 703 is ejected using plunger 402 (method step 1410), in the manner described above. Ejection can be into another container, for further evaluation according to processes known to those of skill in the art. In method step 1412, pipette device 400 can be discarded, or cleaned and sterilized for further use.

As above discussed in regard to FIGS. 4-14, reference is made to several dimensions, including several radii, angles, height, among others. Those of skill in the art can appreciate that although examples of dimensions are provided, these should not be taken in a limiting manner; that is, the aspects of the embodiments are not to be construed as defined or limited by the specific example of the dimensions shown and discussed, but instead are provided merely for illustrating an example of what a device that incorporates the aspects of the embodiments could, in a non-limiting manner, look like.

Furthermore, as those of skill in the art can appreciate, since the aspects of the embodiments are directed towards a physical object, with dimensional characteristics, all of the parts will have various dimensions, some of which are not shown in fulfillment of the dual purposes of clarity and brevity. According to still further aspects of the embodiments, some of these objects will have dimensional characteristics that lend themselves to aesthetic aspects; in fulfillment of the dual purposes of clarity and brevity, dimensions in this regard have also been omitted. Therefore, as the aspects of the embodiments are directed towards a whistling lid for pots used for cooking, it is to be understood that the dimensions of the different objects, some dimensions shown, some dimensions not shown, will be understood by those of skill in the art.

Figure 20:
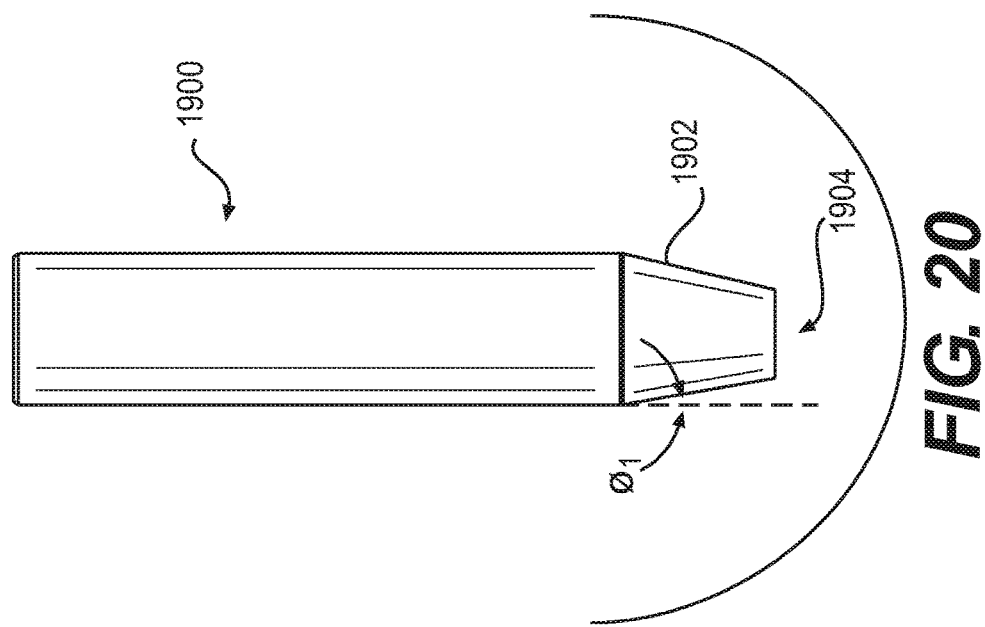
FIGS. 19 and 20 illustrate a perspective and side view, respectively, of a sharpened pipette tube according to aspects of the embodiments.
Figure 19:
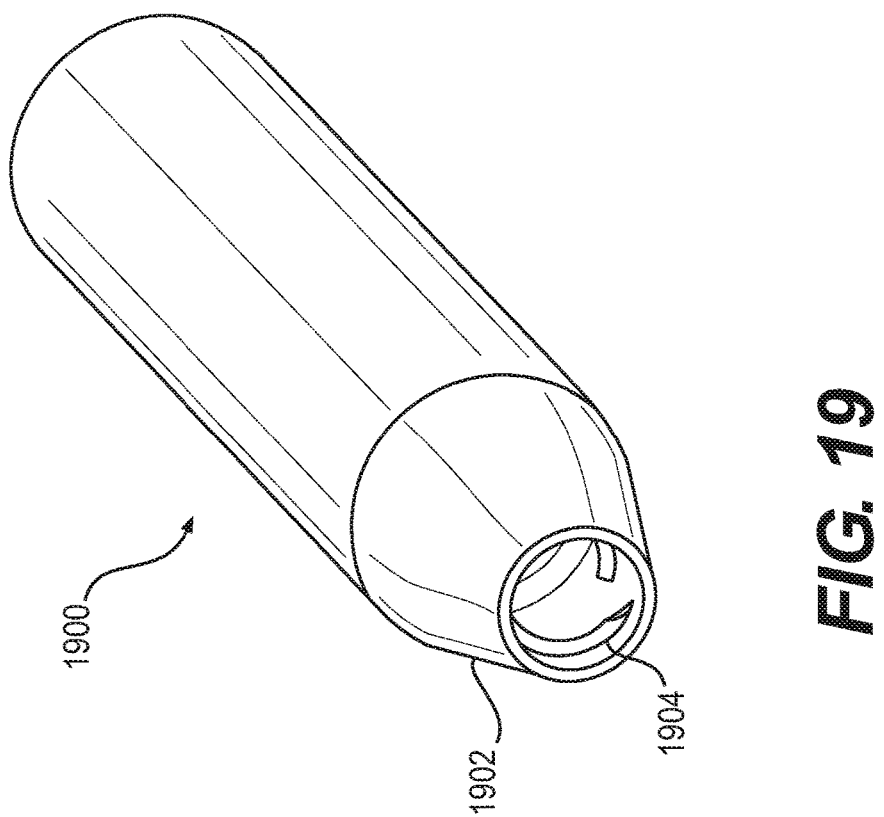

According to further aspects of the embodiments, a handheld solid sample sharpened pipette tube 1900 as shown in FIGS. 19 and 20 comprises a mechanically sharpened pipette tube with an integrated piston. Sharpened pipette tube 1900 can perform the function of both a positive displacement pipette and a biopsy punch. In order to perform its function as a biopsy punch, the end of sharpened pipette tube 1900 needs to be substantially razor sharp and have a thickness at the end of the tip less than about 10 um or less than about 100 um. Since sharpened pipette tube 1900 are typically constructed from plastic, as described herein, and thus injection molded, sharpened pipette tube 1900 can be sharpened following injection molding. The sharpening can be facilitated using an angled planetary cutter, similar to a pencil sharpener, to create a substantially razor sharp edge. The angle formed by the sharpening process is typically between about 70° to about 80°. In the case of sampling solid or semi-solid food item, it can be necessary for the item to be placed on a soft-consumable substrate, such as silicone. During operation, the food item is placed on the substrate and sharpened pipette tube 1900 is pressed through the food item until it touches the substrates or even partially cuts through the substrate producing a cylindrical core of the food item in sharpened pipette tube 1900. The sharpened pipette tube 1900 is then extracted from the food item, and the cylindrical core of the food item can then be ejected into a sample tube using the integrated piston to push out the core according to aspects of the embodiments.

According to further aspects of the embodiments, pipette device 400 can be interfaced, in a substantially similar, albeit different form, with an automated sampling system, such as was described above. Such an automated system would include processor controls, with software and applications for use by operators to control the automated system for sampling solids or high viscosity liquids according to further aspects of the embodiments. The shearing or twisting action needed by shear ring apparatus 410 can be provided by one or more of motors, pneumatic assemblies, and other similar mechanisms, as known by those of skill in the art, with appropriately designed electro-mechanical interfaces. Further, such processor and computer driven control systems can collect and store information about each sampling set, and prepare and provide electronic reports that can then be printed. According to further aspects of the embodiments, such control systems can monitor the automated apparatus itself, and provide reports on status conditions.

Figure 21:
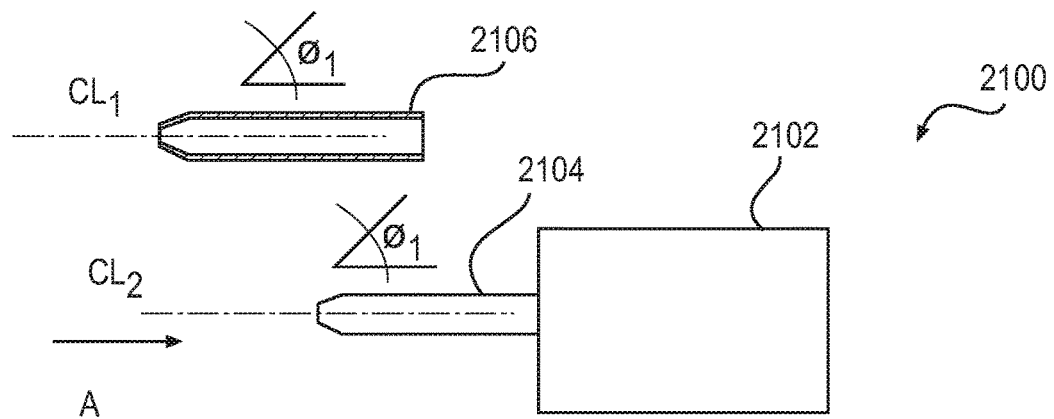
FIG. 21 illustrates a side view of a pipette sharpening apparatus prior to mounting an unsharpened pipette tip according to aspects of the embodiments.

FIG. 21 illustrates a side view of pipette sharpening apparatus (sharpening apparatus) 2100 prior to mounting unsharpened pipette tip 2106 according to aspects of the embodiments. Sharpening apparatus 2100 comprises mount motor (motor) 2102 attached to which is mounting spindle 2104, upon which unsharpened pipette tube (unsharpened pipette) 2106 can be located upon. As shown in FIG. 21, a user can slide unsharpened pipette 2106 over mounting spindle 2104 in the direction of arrow A until unsharpened pipette 2106 is substantially completely fully extended over mounting spindle 2104, in the manner shown in FIG. 22. Mounting spindle 2104 can be made of many different types of metal or other hardened substances, and includes a tip that is conically shaped as shown with an angle $\Theta_1$. Unsharpened pipette 2106 also is formed at an angle of about $\Theta_1$ as can be seen in FIG. 21; angle $\Theta_1$ is in reference to an imaginary centerline of both the unsharpened pipette tip 2106 and mounting spindle 2104 ($CL_1$ for unsharpened pipette 2106, and $CL_2$ for mounting spindle 2104). Implementation of angle $\Theta_1$ for both mounting spindle 2104 and unsharpened pipette 2106 provides a close fit between the two devices, providing for a more efficient grinding and sharpening operation, in that unsharpened pipette 2106 will have a substantially solid surface to be formed against during the grinding operation.

Figure 22:
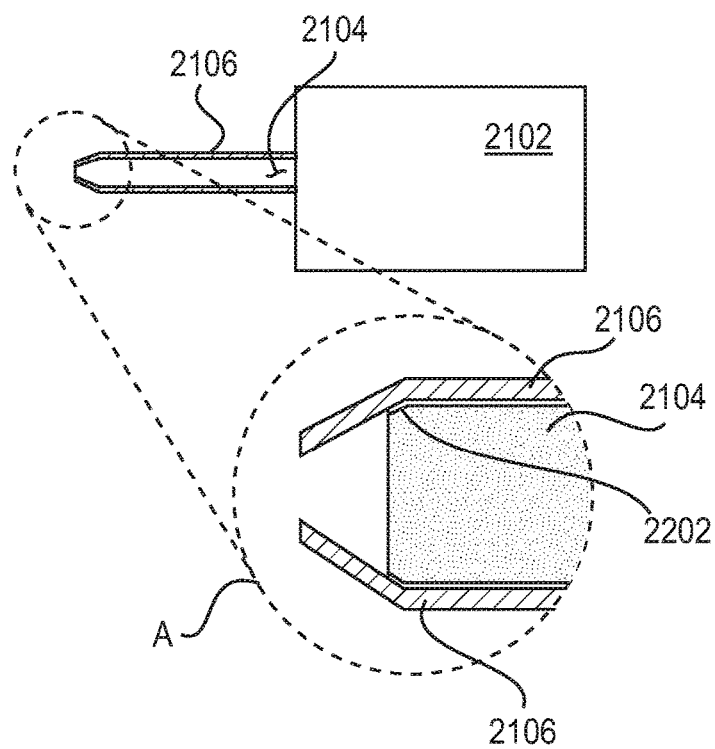
FIG. 22 illustrates a side view of the pipette sharpening apparatus of FIG. 21 following mounting of the unsharpened pipette tip and prior to sharpening.

FIG. 22 illustrates a side view of pipette sharpening apparatus 2100 of FIG. 21 following mounting of unsharpened pipette tip 2106. As those of skill in the art can appreciate, the views of FIGS. 21 and 22 and the structure and function thereof are simplified, and omit many details that are not necessary in regard to the scope of this discussion; nonetheless, those of skill in the art can appreciate that the discussion provides illustrates the various aspects of the embodiments in regard to the manufacture of a sharpened pipette tube as described herein. In addition, there are numerous, if not uncountable variations in the manner of implementing such grinding apparatus and those of skill in the art can appreciate that such variations and equivalents are considered to be within the scope of the aspects of the embodiments.

The close up side view of balloon A of FIG. 22 illustrates how unsharpened pipette 2106 rests on mounting spindle first surface 2202, which is also formed at substantially the same angle $\Theta_1$. Following placement of unsharpened pipette tube 2106 onto mounting spindle 2104, as shown in balloon A of FIG. 22, grinding surface 2302 (shown in FIG. 23) can be moved in close proximity to unsharpened pipette 2106. Motor 2102 can be turned on, thereby spinning mounting spindle 2104 at a predetermined rotational velocity appropriate for the materials and methods involved. Simultaneously the grinding surface 2302 can also be rotated and controlled to provide better control over the process.

Figure 23:
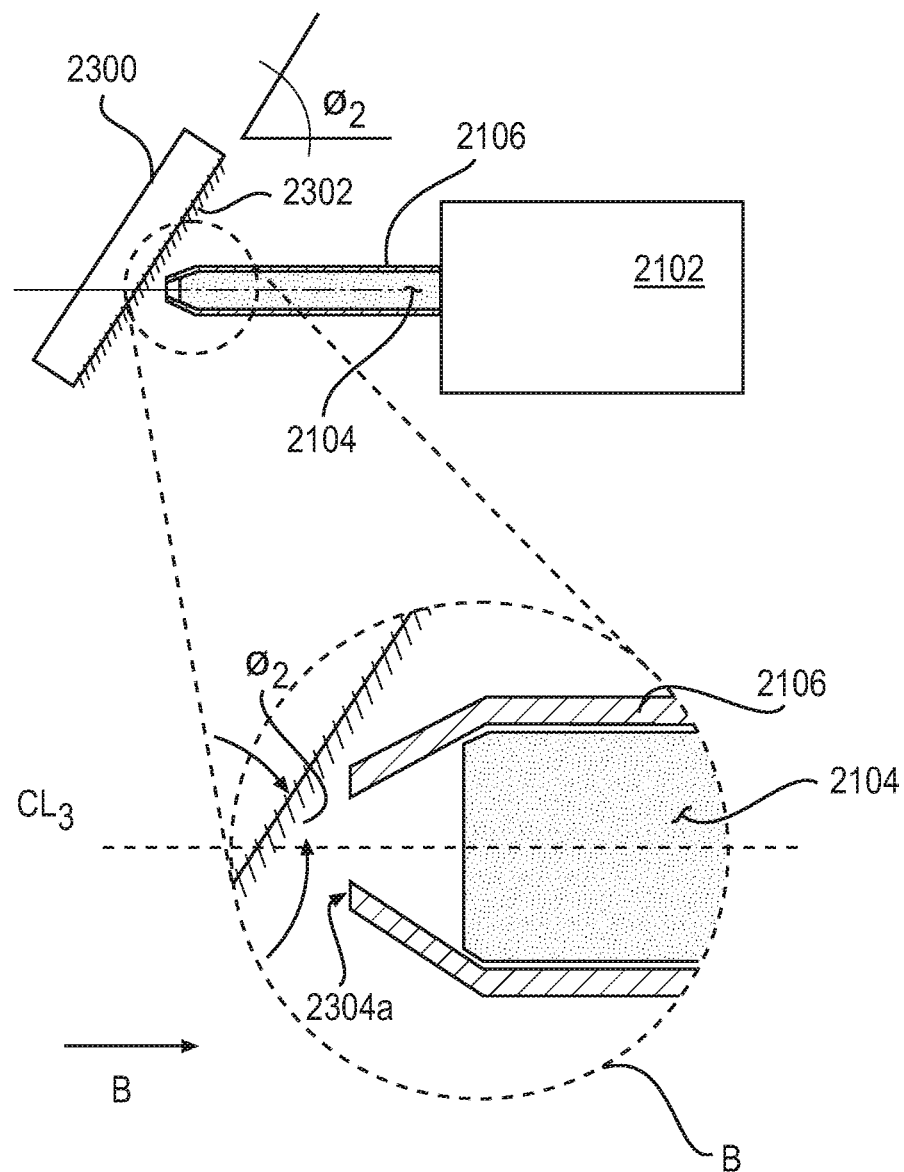
FIG. 23 illustrates a side view of the pipette sharpening apparatus of FIG. 21 following placement of a grinding surface and just prior to sharpening according to aspects of the embodiments.

Referring now to FIG. 23, grinding surface 2302 is placed at angle $\Theta_2$ that can be, according to aspects of the embodiments, larger than $\Theta_1$. As shown in balloon B of FIG. 23, which is a close-up side view of grinding surface 2302 and unsharpened pipette 2106 on mounting spindle 2104, angle $\Theta_2$ is also formed about a centerline, in this case, the centerline $CL_3$ of grinding surface 2302. Further shown in the close-up side view of balloon B of FIG. 23 is pipette tip contact surface (contact surface) 2304a. Contact surface 2304a is the unsharpened tip of pipette 2106; it is substantially flat, meaning that it forms about an angle of zero degrees with respect to a sample surface in unsharpened pipette 2106 were to be used to try and obtain a sample.

Figure 24A:
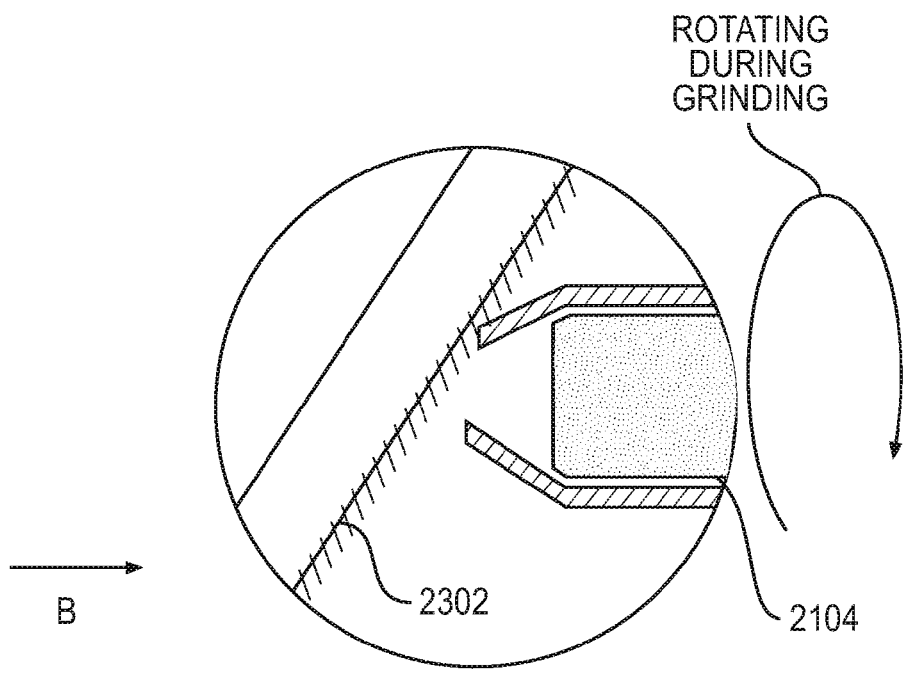
FIG. 24A illustrates a close up side view of the pipette sharpening apparatus of FIG. 23 with the grinding surface sharpening the unsharpened pipette tip.
Figure 24B:
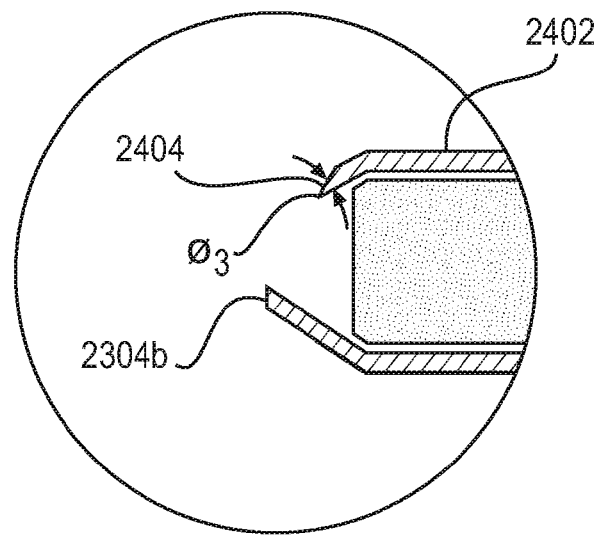
FIG. 24B illustrates a close up side view of the pipette tip following sharpening.

Sharpening, as shown in FIGS. 24A and 24B, occurs when unsharpened pipette 2106 is rotated by mount motor 2102, and grinding surface is place in contact with the tip of unsharpened pipette 2106. After mounting spindle 2104 is rotating at its predetermined rotational velocity, grinding surface 2302 can be moved in the direction of arrow B (or, motor 2102 can be moved, if sharpening apparatus is so configured), until grinding surface 2302 is placed in contact with the tip of unsharpened pipette 2106, and begins removing the material (for example, a plastic material) until the sharpened tip is formed. The basic grinding method may be according to those recognized by skilled persons, and/or may be accomplished manually, automatically with the addition of computer controlled machinery and/or optical measurement devices, or a combination of the latter. Any and all such variations and equivalents of sharpening apparatus 2100 are within the scope of the aspects of the embodiments. The result of the sharpening process is sharpened pipette 2402, as seen in FIG. 24B.

Referring now to FIG. 24B, it can be seen that second pipette tip sample contact surface (second contact surface) 2304b has been formed as a result of the sharpening process. Second contact surface is formed at an angle of $\Theta_3$ as shown in FIG. 24B; $\Theta_3$ is the difference between $\Theta_1$ and $\Theta_2$ ($\Theta_2 - \Theta_1 = \Theta_3$). Thus, a relative sharp angle can be formed at the tip of newly formed sharpened pipette 2402. According to aspects of the embodiments, $\Theta_1$ can range from about 0° to about 45°, $\Theta_2$ can range from about 1° to about 90°, and therefore, $\Theta_3$ can range from about 1° to about 90°. According to further aspects of the embodiments, $\Theta_3$ can range between about 10° to about 30° to create a robust knife edge. Such angles are dependent upon the materials of which unsharpened pipette 2106 is made, and grinding surface 2302, among other factors.

FIG. 25A illustrates a cross-sectional view of conventional direct injection molding system 2500 that can be used to create a conventional pipette, and FIG. 25B illustrates a close-up cross-sectional view of a tip portion of the direct injection molding system of FIG. 25A. As shown in FIG. 25B, the mold forms the conventional tip that, while narrowed to form an angled tip of about $\Theta_1$, does not provide the sharpened second pipette tip sample contact surface 2304b as described above in regard to FIG. 23, among others, according to aspects of the embodiments.

As shown and described in regard to FIGS. 21-24, a first means for preparing sharpened pipette tube 2402 was presented. FIG. 25A illustrates conventional direct injection-molding system (first molding system) 2500 that can be used to create the unsharpened pipette 2106 according to known direct injection molding techniques. The first mold includes an outer mold and inner mold, channels through which melted material, such as plastic, can flow, as well as thermocouples, cooling channels, and other features known to those of skill in the art to manufacture direct injection molded components. As skilled persons can appreciate, the illustration and accompanying description of FIGS. 25A and 25B are greatly simplified for the purpose of brevity and clarity only, as some of these details have been omitted.

Attention is now directed towards FIGS. 26A and 26B, which illustrate second direct injection molding system (second molding system) 2600 according to an aspect of the embodiments, which can be used as a different method for the manufacture of sharpened pipette 2402. A sharpened pipette 2402 manufactured using second molding system 2600 will have substantially identical features as one manufactured by pipette sharpening apparatus 2100. In operation, and as mentioned above, this discussion is simplified. A suitable mold can be formed by as little as two parts for creating sharpened pipette tube 2402 via a direct injection molding process. Second molding system 2600 comprises second molding system outer mold (outer mold) 2602, second molding system inner mold (inner mold) 2604, and second molding system insert (insert) 2606 according to aspects of the embodiments. Inner and outer molds 2602, 2604 can be substantially similar to that of the corresponding inner and outer molds of first molding system 2500; outer mold 2602 and inner mold 2604 can be fashioned from a suitable material, such as steel, with the appropriate channels for allowing hot melted plastic to flow through (not shown). As those of skill in the art can appreciate, both first and second injection molded systems 2500, 2600 such as the ones shown in FIGS. 25A, 25B, 26A, and 26B, would normally further include heating and cooling channels, and perhaps even air channels to assist in releasing the part once it is has been formed and cooled sufficiently. In order to determine when such cooling has occurred, a suitable number and type of thermocouples can also be appropriately located therein, as those of skill in the art can appreciate. The manner of injecting the hot melted plastic typically comprises an injection jet (not shown) through which the hot melted plastic can flow in a substantially uniform and controlled manner. As with the grinding apparatus described above in regard to FIGS. 21-24, such injection molding devices as briefly described and shown here can be manually controlled, but are much more often highly sophisticated machines with accompanying computer and processor driven devices to control the creation of the parts substantially automatically.

When joined together in the manner as shown in FIG. 26A, a cavity is formed around inner mold 2604 into which hot melted plastic can be injected at relatively high pressures through a channel in a manner known to those of skill in the art. According to aspects of the embodiments, however, the outer and inner molds 2602, 2604, when so joined (using retention pings (not shown)), along with insert 2606, form the shape of the sharpened pipette tube 2402 by forming outer and inner molds 2602, 2604, to include the angle $\Theta_3$ as shown in detail in FIG. 26B, which is a close-up cross sectional view of the tip portion of second molding system 2600 according to aspects of the embodiments.

Following cooling, which can occur over time via dissipation through the mold parts, or through cooling channels (not shown), or combination of the two, the molded sharpened pipette tube 2402 can be ejected in a manual or automatic manner (the latter using cooling air, or cooling liquids, such as water, among others). It should be noted that the space between outer mold 2602 and inner mold 2604 forms the injection molded pipette tube, and the distance d as shown in FIG. 26A is the thickness of the pipette tube, with the exception of some shrinkage due to cooling, as known to those of skill in the art. Such distance d can further take into account such cooling shrinkage, should it occur. Such shrinkage can be dependent on numerous factors, such as the rate of cooling, and materials used to make the injection molded pipette tube. Once so manufactured, the "sharpened" pipette tube can be used substantially similar as to any of the previously described sharpened pipette tubes.

Figure 27:
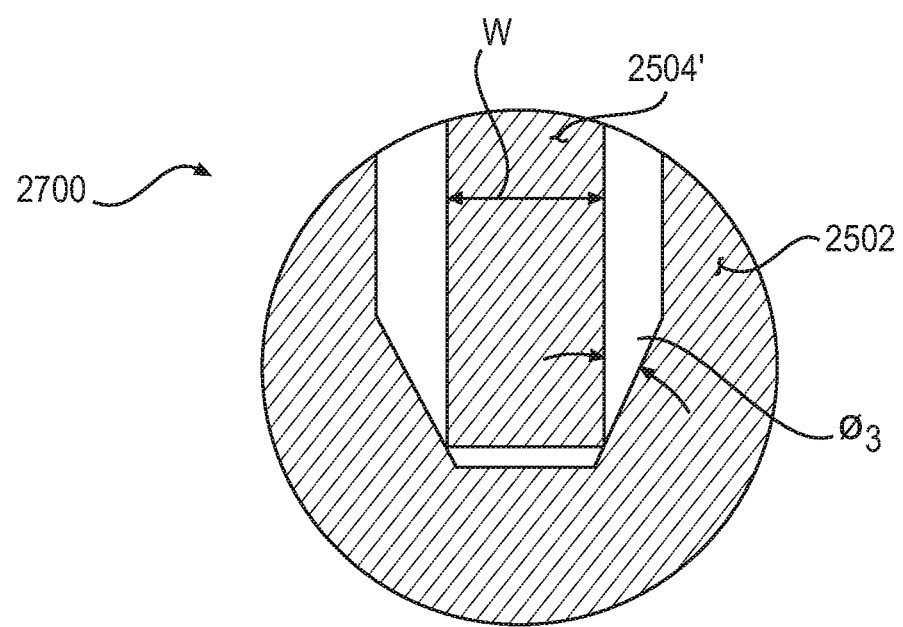
FIG. 27 illustrates a close-up cross-sectional view of a tip portion of a direct injection molding system that can be used to create a sharpened pipette according to further aspects of the embodiments.

FIG. 27 illustrates a close-up cross-sectional view of a tip portion of third direct injection molding system (third molding system) 2700 that can be used to create a sharpened pipette according to further aspects of the embodiments. Third molding system 2700 includes outer mold 2602 and modified inner mold 2604' according to aspects of the embodiments. The width of inner mold 2604' is made wider in the third molding system 2700, and abuts an inner wall portion of outer mold 2604 in the manner shown in FIG. 27 to create angle $\Theta_3$ at second pipette tip sample contact surface 2304b, substantially similarly to that as manufactured in the various aspects previously presented.

Figure 28:
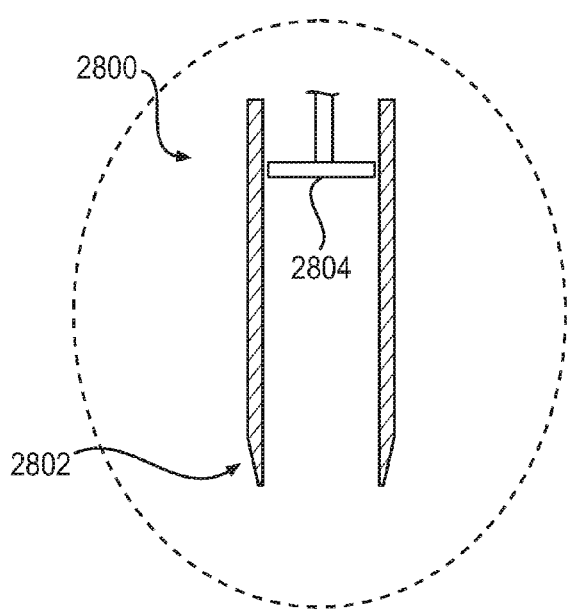
FIG. 28 illustrates a conventional biopsy punch system.
Figure 29:
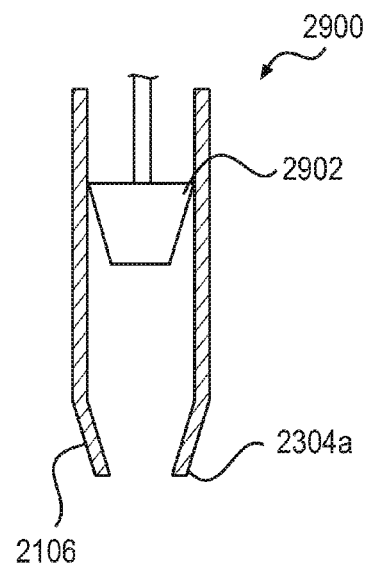
FIG. 29 illustrates a positive displacement pipette system.
Figure 30:
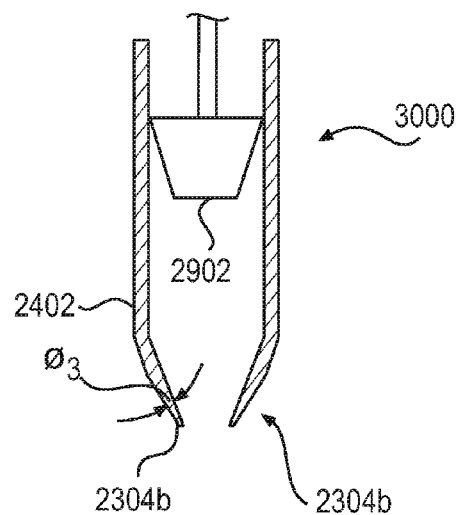
FIG. 30 illustrates a hybrid positive displacement-biopsy punch system according to an aspect of the embodiments using a pipette sharpened using the systems, methods, and modes according to aspects of the embodiments.

Attention is now directed towards FIGS. 28, 29, and 30. FIG. 28 illustrates a conventional biopsy punch system 2800, FIG. 29 illustrates a conventional positive displacement pipette system 2900, and FIG. 30 illustrates a hybrid positive displacement pipette-biopsy punch system 3000 according to an aspect of the embodiments using sharpened pipette 2402 that includes second contact surface 2304b formed at an angle of $\Theta_3$. As described above $\Theta_3$ is a relatively sharp angle compared to the angles formed by first contact surface 2403a, and is formed using the systems, methods, and modes according to aspects of the embodiments previously discussed and described herein.

In certain embodiments, the various functional aspects of the foregoing embodiments are embodied in a fully or semi-automated system driven in whole or in part by one or more processors, whether part of the automated assembly, or remotely located or both. Exemplary robotic systems for pipetting, as above described, and for automating the actions of the pipette and related elements, and other automated or semi-automated systems and processes, may be used in coordination with the foregoing embodiments, and employ resident or remote computer processing hardware or software. These embodiments are described with some particularity below, though skilled persons will realize that many other implementations can be used within the context of and without departing from the present teachings.

In particular, certain embodiments take the form of an entirely hardware embodiment or an embodiment combining hardware and software aspects. Further, the embodiments can take the form of a non-transitory computer program product stored on a computer-readable storage medium having computer-readable instructions embodied in the medium. Any suitable computer-readable medium can be utilized, including hard disks, CD-ROMs, digital versatile discs (DVDs), optical storage devices, or magnetic storage devices such a floppy disk or magnetic tape. Other non-limiting examples of computer-readable media include flash-type memories or other known types of memories.

Further, those of ordinary skill in the art in the field of the embodiments can appreciate that such functionality can be designed into various types of circuitry, including, but not limited to field programmable gate array structures (FPGAs), application specific integrated circuitry (ASICs), microprocessor based systems, among other types. A detailed discussion of the various types of physical circuit implementations does not substantively aid in an understanding of the embodiments, and as such has been omitted for the dual purposes of brevity and clarity. However, as well known to those of ordinary skill in the art, the systems and methods discussed herein can be implemented as discussed, and can further include programmable devices.

Such programmable devices and/or other types of circuitry as previously discussed can include a processing unit, a system memory, and a system bus that couples various system components including the system memory to the processing unit. The system bus can be any of several types of bus structures including a memory bus or memory controller, a peripheral bus, and a local bus using any of a variety of bus architectures. Furthermore, various types of computer readable media can be used to store programmable instructions. Computer readable media can be any available media that can be accessed by the processing unit. By way of example, and not limitation, computer readable media can comprise computer storage media and communication media. Computer storage media includes volatile and non-volatile as well as removable and non-removable media implemented in any method or technology for storage of information such as computer readable instructions, data structures, program modules or other data. Computer storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other medium which can be used to store the desired information and which can be accessed by the processing unit. Communication media can embody computer readable instructions, data structures, program modules or other data in a modulated data signal such as a carrier wave or other transport mechanism and can include any suitable information delivery media.

The system memory can include computer storage media in the form of volatile and/or nonvolatile memory such as read only memory (ROM) and/or random access memory (RAM). A basic input/output system (BIOS), containing the basic routines that help to transfer information between elements connected to and between the processor, such as during start-up, can be stored in memory. The memory can also contain data and/or program modules that are immediately accessible to and/or presently being operated on by the processing unit. By way of non-limiting example, the memory can also include an operating system, application programs, other program modules, and program data.

The processor can also include other removable/non-removable, volatile/nonvolatile, and transitory/non-transitory computer storage media. For example, the processor can access a hard disk drive that reads from or writes to non-removable, nonvolatile, and non-transitory magnetic media, a magnetic disk drive that reads from or writes to a removable, nonvolatile, and non-transitory magnetic disk, and/or an optical disk drive that reads from or writes to a removable, nonvolatile, and non-transitory optical disk, such as a CD-ROM or other optical media. Other removable/non-removable, volatile/nonvolatile, and non-transitory computer storage media that can be used in the operating environment include, but are not limited to, magnetic tape cassettes, flash memory cards, digital versatile disks, digital video tape, solid state RAM, solid state ROM and the like. A hard disk drive can be connected to the system bus through a non-removable memory interface such as an interface, and a magnetic disk drive or optical disk drive can be connected to the system bus by a removable memory interface, such as an interface.

The embodiments discussed herein can also be embodied as computer-readable codes on a computer-readable medium. The computer-readable medium can include a computer-readable recording medium and a computer-readable transmission medium. The computer-readable recording medium is any data storage device that can store data which can be thereafter read by a computer system. Examples of the computer-readable recording medium include read-only memory (ROM), random-access memory (RAM), CD-ROMs and generally optical data storage devices, magnetic tapes, flash drives, and floppy disks. The computer-readable recording medium can also be distributed over network coupled computer systems so that the computer-readable code is stored and executed in a distributed fashion. The computer-readable transmission medium can transmit carrier waves or signals (e.g., wired or wireless data transmission through the Internet). Also, functional programs, codes, and code segments to, when implemented in suitable electronic hardware, accomplish or support exercising certain elements of the appended claims can be readily construed by programmers skilled in the art to which the embodiments pertains.

Although the features and elements of aspects of the embodiments are described being in particular combinations, each feature or element can be used alone, without the other features and elements of the embodiments, or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and can include other examples that occur to those skilled in the art. Such other examples are intended to be within the scope of the claims.

The above-described embodiments are intended to be illustrative in all respects, rather than restrictive, of the embodiments. Thus the embodiments are capable of many variations in detailed implementation that can be derived from the description contained herein by a person skilled in the art. No element, act, or instruction used in the description of the present application should be construed as critical or essential to the embodiments unless explicitly described as such. Also, as used herein, the article "a" is intended to include one or more items.

All United States patents and applications, foreign patents, and publications, if any, discussed above are hereby incorporated herein by reference in their respective entireties.

We claim:

1. A handheld pipette material sampling device comprising:
    a pipette tube,
    the pipette tube being adapted to be matingly attached to
        a plunger device, the plunger device comprising:
        a handle;
        a plunger; and
        a piston,
    within a shell of the device;
    a spring being positioned to return the plunger to a non-depressed position following depression of the plunger; and
    a shear ring apparatus matingly attached to the pipette tube, comprising
        a shear ring tube portion, a plurality of shear ring teeth, and a knobbed plate for rotating the shear ring.

2. The handheld pipette material sampling device according to claim 1, wherein the shear ring tube portion is enabled to slidingly engage about the pipette tube, and slide over the pipette tube into the sample following said insertion of the pipette tube with sharpened teeth into any of a said solid material, a said high viscosity liquid, and a said substantially solid material.

3. The handheld pipette material sampling device according to claim 2, the shear ring teeth being engagably enabled to pierce the sample.

4. The handheld pipette material sampling device according to claim 3, the shear ring apparatus being rotatably enabled to rotate in any one of a clockwise and a counterclockwise direction at a certain point of insertion such that the shear ring teeth sever a portion of any said material to be sampled.

5. The handheld pipette material sampling device according to claim 3, the pipette tube being enabled to retain any one of a severed portion and a sheared off portion for any one of removal and analysis thereof.

6. The handheld pipette material sampling device according to claim 1, wherein the shear ring apparatus and the remaining portion of the handheld device comprising a main body portion are enabled to be packaged as a single assembly device such that a user of the handheld device need not assemble such handheld device before use thereof.

7. The handheld pipette material sampling device according to claim 1, wherein the handheld device being enabled for sampling of any one of: a muscle tissue; a food in any one of a simple form comprising a single type of material and a complex form comprising any combination of simple form materials.

8. The handheld pipette material sampling device according to claim 1, wherein the sample obtained by the handheld device is amenable to any one of a deoxyribonucleic acids related testing, a mass spectrometry related testing, and chromatography related testing.

9. The handheld pipette material sampling device according to claim 1, wherein the handheld device is operable to obtain the said sample comprising an amount in the range of about 20 milligrams to about 200 milligrams, said range depending upon the density of the said sample.

10. The handheld pipette material sampling device according to claim 1, wherein
    the plurality of shear ring teeth are adapted to pierce the sample, the sample comprising any one of:
        a solid material;
        a high viscosity liquid material; and
        a substantially solid material.

11. The handheld pipette material sampling device according to claim 1 wherein
    the handheld device is further enabled to eject the material from the pipette tube by operation of the spring.

12. A method of extracting a sample with a handheld pipette material sampling device, comprising:
- enabling a pipette tube that is part of the handheld device to pierce the sample;
- enabling depression of a plunger of a plunger device, the plunger being adapted to be matingly attached to the pipette tube, and comprising: a handle; said plunger; and a piston, within a shell of the plunger device; and
- enabling a spring to return the plunger to a non-depressed position following a said depression of the plunger, and wherein
  - the handheld device further comprises a shear ring apparatus matingly attached to the pipette tube, comprising
    - a shear ring tube portion, a plurality of shear ring teeth, and a knobbed plate for rotating the shear ring, the shear ring apparatus being enabled to pierce the sample.

13. The method of extracting a sample according to claim 12, wherein the shear ring tube portion is enabled to slidingly engage about the pipette tube, and slide over the pipette tube into the sample following said insertion of the pipette tube into any of a said material.

14. The method of extracting a sample according to claim 13, the shear ring teeth being engagably enabled to perform said piercing of the sample.

15. The method of extracting a sample according to claim 14, the shear ring apparatus being rotatably enabled to rotate in any one of a clockwise and a counter-clockwise direction at a certain point of insertion such that the shear ring teeth sever a portion of any said material to be sampled.

16. The method of extracting a sample according to claim 14, the pipette tube being enabled to retain any one of a severed portion and a sheared off portion for any one of removal and analysis thereof.

17. The method of extracting a sample according to claim 12, wherein the shear ring apparatus and the remaining portion of the handheld device comprising a main body portion are enabled to be packaged as a single assembly device such that a user of the handheld device need not assemble such handheld device before use thereof.

18. The method of extracting a sample according to claim 12, wherein the handheld device being enabled for sampling of any one of: a muscle tissue; a food in any one of a simple form comprising a single type of material and a complex form comprising any combination of simple form materials.

19. The method of extracting a sample according to claim 12, wherein the sample being obtained by the handheld device is amenable to any one of a deoxyribonucleic acids related testing, a mass spectrometry related testing, and chromatography related testing.

20. The method of extracting a sample according to according to claim 12, wherein the handheld device is operable to obtain the said sample comprising an amount in the range of about 20 milligrams to about 200 milligrams, said range depending upon the density of the said sample.

21. The method according to claim 12, wherein
the plurality of shear ring teeth are adapted to pierce the sample, the sample comprising any one of:
- a solid material;
- a high viscosity liquid material; and
- a substantially solid material.

22. The method according to claim 12, further comprising:
- ejecting the material from the pipette tube by operation of the spring.

* * * * *